(12) United States Patent
Devon et al.

(10) Patent No.: US 9,056,313 B2
(45) Date of Patent: Jun. 16, 2015

(54) CATALYSTS FOR THE PRODUCTION OF HYDROXY ETHER HYDROCARBONS BY VAPOR PHASE HYDROGENOLYSIS OF CYCLIC ACETALS AND KETALS

(75) Inventors: Thomas James Devon, Longview, TX (US); Damon Ray Billodeaux, Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 410 days.

(21) Appl. No.: 13/168,349

(22) Filed: Jun. 24, 2011

(65) Prior Publication Data
US 2012/0330067 A1 Dec. 27, 2012

(51) Int. Cl.
| | | |
|---|---|---|
| *C07C 41/28* | (2006.01) |
| *B01J 35/10* | (2006.01) |
| *B01J 23/44* | (2006.01) |
| *B01J 23/58* | (2006.01) |
| *B01J 37/28* | (2006.01) |
| *B01J 21/02* | (2006.01) |
| *B01J 21/08* | (2006.01) |
| *B01J 27/13* | (2006.01) |
| *B01J 27/138* | (2006.01) |
| *B01J 21/12* | (2006.01) |
| *B01J 31/38* | (2006.01) |
| *B01J 21/06* | (2006.01) |
| *B01J 31/26* | (2006.01) |
| *B01J 21/04* | (2006.01) |

(52) U.S. Cl.
CPC .............. *B01J 35/1014* (2013.01); *B01J 21/04* (2013.01); *B01J 21/066* (2013.01); *B01J 23/44* (2013.01); *B01J 23/58* (2013.01); *B01J 37/28* (2013.01); *B01J 35/1009* (2013.01); *C07C 41/28* (2013.01)

(58) Field of Classification Search
CPC ...... B01J 31/0232; B01J 31/143; B01J 21/04; B01J 21/066
USPC .......... 568/678; 502/170, 226, 162, 327, 328, 502/230, 339, 349
See application file for complete search history.

(56) References Cited

U.S. PATENT DOCUMENTS

| | | | |
|---|---|---|---|
| 2,425,042 A | 8/1947 | McNamee et al. | |
| 2,429,878 A | 10/1947 | Gresham et al. | |
| 2,486,024 A | 10/1949 | Hearne et al. | |
| 3,275,680 A * | 9/1966 | Holzrichter et al. | 560/243 |
| 4,024,159 A | 5/1977 | Peterson | |
| 4,038,175 A | 7/1977 | Bhasin | |
| 4,062,898 A | 12/1977 | Dubeck et al. | |
| 4,071,568 A | 1/1978 | Onoda et al. | |
| 4,088,700 A | 5/1978 | Watts | |
| 4,169,959 A | 10/1979 | Arpe | |
| 4,308,403 A | 12/1981 | Knifton | |
| 4,317,943 A | 3/1982 | Knifton | |
| 4,356,327 A | 10/1982 | Knifton | |
| 4,357,477 A | 11/1982 | Knifton | |
| 4,375,394 A | 3/1983 | Devon | |
| 4,390,734 A | 6/1983 | Knifton | |
| 4,430,253 A | 2/1984 | Dubeck | |
| 4,435,595 A | 3/1984 | Agreda et al. | |
| 4,478,017 A | 10/1984 | Brown et al. | |
| 4,479,017 A | 10/1984 | Ayusawa et al. | |
| 4,482,753 A | 11/1984 | Huang et al. | |
| 4,484,009 A | 11/1984 | Ghenassia et al. | |
| 4,537,980 A | 8/1985 | Greenshields | |
| 4,568,780 A | 2/1986 | Knifton | |
| 4,617,287 A | 10/1986 | Lyons | |
| 4,618,729 A | 10/1986 | Duggan et al. | |
| 4,663,489 A | 5/1987 | Duggan et al. | |
| 4,692,426 A | 9/1987 | Duggan et al. | |
| 4,847,425 A | 7/1989 | Degner et al. | |
| 4,895,818 A | 1/1990 | Duggan et al. | |
| 4,895,987 A | 1/1990 | Duggan et al. | |
| 4,939,294 A | 7/1990 | Agreda et al. | |
| 5,319,148 A * | 6/1994 | Karcher et al. | 568/653 |
| 5,362,918 A | 11/1994 | Aizawa et al. | |
| 5,399,631 A | 3/1995 | Egawa et al. | |
| 5,446,208 A | 8/1995 | Koshino et al. | |
| 5,446,210 A | 8/1995 | Hees et al. | |
| 5,523,491 A | 6/1996 | Egawa et al. | |
| 5,589,597 A | 12/1996 | Egawa et al. | |
| 5,616,736 A | 4/1997 | Thigpen | |
| 5,720,895 A | 2/1998 | Nakagawa et al. | |

(Continued)

FOREIGN PATENT DOCUMENTS

| | | |
|---|---|---|
| CA | 1 254 190 | 5/1989 |
| DE | 419223 C | 9/1925 |
| DE | 3328561 A1 | 2/1985 |
| DE | 238 232 A1 | 8/1986 |
| DE | 19648960 A1 | 5/1998 |
| DE | 10036423 A1 | 3/2001 |
| EP | 0 168 989 A1 | 1/1986 |
| EP | 0 169 666 B1 | 1/1986 |
| EP | 0 271 091 A1 | 6/1988 |
| EP | 0 312 659 A1 | 4/1989 |

(Continued)

OTHER PUBLICATIONS

Coelho, Antonio Carlos Vieira, et al.; "Surface Area, Crystal Morphology and Characterization of Transition Alumina Powders from a New Gibbsite Precursor"; Materials Research, vol. 10, No. 2, pp. 183-189, (2007), XP002683656.

(Continued)

*Primary Examiner* — Rosalynd Keys
(74) *Attorney, Agent, or Firm* — Phan Law Group PLLC

(57) ABSTRACT

Catalyst compositions of palladium supported on alumina or zirconium oxide supports having low or no silicon dioxide contents and having a specific surface area or modified with alkali, alkaline earth, or phosphine oxide compounds are selective in a vapor phase hydrogenolysis reaction to convert cyclic acetal compounds and/or cyclic ketal compounds in the presence of hydrogen to their corresponding hydroxy ether hydrocarbon reaction products.

63 Claims, No Drawings

(56) References Cited

U.S. PATENT DOCUMENTS

| | | | |
|---|---|---|---|
| 5,763,691 A | 6/1998 | Kawabe et al. | |
| 5,780,687 A | 7/1998 | Holderich et al. | |
| 5,821,391 A | 10/1998 | Holderich et al. | |
| 5,866,735 A | 2/1999 | Cheung et al. | |
| 5,886,198 A | 3/1999 | Ogawa et al. | |
| 5,917,059 A | 6/1999 | Bruchmann et al. | |
| 5,935,896 A * | 8/1999 | Dupuis et al. | 502/439 |
| 6,013,844 A | 1/2000 | Heineke et al. | |
| 6,015,875 A | 1/2000 | Smith et al. | |
| 6,028,215 A | 2/2000 | Bessling et al. | |
| 6,080,897 A | 6/2000 | Kawabe | |
| 6,087,539 A | 7/2000 | Yamasaki et al. | |
| 6,124,479 A | 9/2000 | Hinoue et al. | |
| 6,136,576 A | 10/2000 | Diaz-Torres | |
| 6,143,908 A | 11/2000 | Hinoue et al. | |
| 6,166,240 A | 12/2000 | Jiang et al. | |
| 6,207,850 B1 | 3/2001 | Jiang et al. | |
| 6,232,512 B1 | 5/2001 | Haas et al. | |
| 6,265,623 B1 | 7/2001 | Morawietz et al. | |
| 6,291,725 B1 | 9/2001 | Chopade | |
| 6,380,419 B2 | 4/2002 | Kawabe | |
| 6,458,992 B1 | 10/2002 | Lederer et al. | |
| 6,518,464 B2 | 2/2003 | Therre et al. | |
| 6,548,681 B1 | 4/2003 | Chopade et al. | |
| 6,657,089 B1 | 12/2003 | Nagasawa et al. | |
| 6,670,489 B2 | 12/2003 | Koyama et al. | |
| 6,713,640 B2 | 3/2004 | Miller et al. | |
| 6,969,779 B2 | 11/2005 | Brewer et al. | |
| 7,030,277 B2 | 4/2006 | Groten et al. | |
| 7,060,372 B2 | 6/2006 | Fryd et al. | |
| 7,071,362 B2 | 7/2006 | Sugawara et al. | |
| 7,160,524 B2 | 1/2007 | Lederer et al. | |
| 7,301,055 B2 | 11/2007 | Hoffmockel et al. | |
| 7,488,851 B2 | 2/2009 | Egidio Rodrigues et al. | |
| 7,498,451 B2 | 3/2009 | Haderlein et al. | |
| 7,534,922 B2 | 5/2009 | Gorling et al. | |
| 7,754,900 B2 | 7/2010 | Siegert et al. | |
| 2003/0187281 A1 | 10/2003 | Miller et al. | |
| 2006/0129000 A1 | 6/2006 | Goring et al. | |
| 2008/0283384 A1 | 11/2008 | Lang et al. | |
| 2010/0048940 A1 | 2/2010 | Tulchinsky et al. | |
| 2010/0099894 A1 | 4/2010 | Dubois et al. | |
| 2010/0158780 A1 * | 6/2010 | Galligan et al. | 423/239.1 |
| 2010/0228065 A1 | 9/2010 | Cheung et al. | |
| 2010/0261936 A1 | 10/2010 | Okumura et al. | |
| 2010/0292491 A1 | 11/2010 | Selifonov et al. | |
| 2011/0034739 A1 | 2/2011 | Stochniol et al. | |
| 2011/0207969 A1 | 8/2011 | Olken et al. | |

FOREIGN PATENT DOCUMENTS

| | | |
|---|---|---|
| EP | 0499055 A2 | 8/1992 |
| EP | 0616994 A2 | 9/1994 |
| EP | 0 624 563 A1 | 11/1994 |
| EP | 0696564 A1 | 2/1996 |
| EP | 1 236 511 A1 | 9/2002 |
| FR | 2 906 246 A1 | 3/2008 |
| GB | 1020500 A | 2/1966 |
| JP | 52073810 A | 6/1977 |
| JP | 56166186 A | 12/1981 |
| JP | 58198431 A | 11/1983 |
| JP | 5155878 A | 6/1993 |
| JP | 5271217 A | 10/1993 |
| JP | 6128184 A | 5/1994 |
| JP | 2001072636 A | 3/2001 |
| JP | 4287546 B2 | 7/2009 |
| WO | WO 01/19763 A1 | 3/2001 |
| WO | WO 03/002547 A1 | 1/2003 |
| WO | WO 2010/027663 A1 | 3/2010 |

OTHER PUBLICATIONS

Hudson, L. Keith, et al.; "Aluminum Oxide", Internet Citation XP-002596245, pp. 1-40, Jun. 15, 2000, URL: http://onlinelibrary.wiley.com/doi/10.

Hibbert, H., et al.: Studies on the reactions relating to carbohydrates and polysaccharides. X. Synthesis and relative stability of cyclic acetals from 1, 2- and 1, 3-glycols; Journal of the American Chemistry Society, vol. 46, No. 5, 1924. pp. 1283-1290, XP002621973, cited in the application pp. 1286, 1287, "Experimental Part".

Notification of Transmittal of the International Search Report and the Written Opinion of the International Searching Authority dated Jun. 19, 2012 for International Application No. PCT/US2012/043085.

Notification of Transmittal of the International Search Report and the Written Opinion of the International Searching Authority dated Jun. 14, 2012 for International Application No. PCT/US2012/042378.

Notification of Transmittal of the International Search Report and the Written Opinion of the International Searching Authority dated Jun. 8, 2012 for International Application No. PCT/US2012/041459.

Notification of Transmittal of the International Search Report and the Written Opinion of the International Searching Authority dated Sep. 3, 2012 for International Application No. PCT/US2012/042458.

Notification of Transmittal of the International Search Report and the Written Opinion of the International Searching Authority dated Sep. 11, 2012 for International Application No. PCT/US2012/043071.

Notification of Transmittal of the International Search Report and the Written Opinion of the International Searching Authority dated Oct. 15, 2012 for International Application No. PCT/US2012/042453.

Notification of Transmittal of the International Search Report and the Written Opinion of the International Searching Authority dated Sep. 14, 2012 for International Application No. PCT/US2012/043093.

USPTO Office Action dated Nov. 9, 2012 for co-pending U.S. Appl. No. 13/168,374.

USPTO Office Action dated Nov. 26, 2012 for co-pending U.S. Appl. No. 13/168,229.

Knifton "Syngas reactions: Part VIII: The preparation of glycol monoalkyl ethers," Journal of Molecular Catalysis 1985, 30, pp. 281-297.

Jakab et al. "Synthesis, regioselective hydrogenolysis, partial hydrogenation, and conformational study of dioxane and dkoxane-type (9-anthracenyl)methylene acetals of sugars," Carbohydrate Research 2009, 344, pp. 2444-2453.

Broekhuis et al. "Recovery of Propylene Glycol from Dilute Aqueous Solutions via Reversible Reaction with Aldehydes" Ind. Eng. Chem. Res. 1994, 33, pp. 3230-3237.

Dhale et al. "Propylene Glycol and Ethylene Glycol Recovery from Aqueous Solution via Reactive Distillation" Chemical Engineering Science, 2004, 59, pp. 2881-2890.

Hao et al. "Downstream processing of 1,3-propanediol fermentation broth" J. Chem. Technol. Biotechnol. 2006, 81, pp. 102-108.

Howard et al. "Hydrogenolysis of Ketals" J. Org. Chem., 1961 26(4), pp. 1026-1028.

Osman et al. "Cyclic Acetal Formation Between 2-Pyridinecarboxaldehyde and y-Hydroxy-a,b-Acetylenic Esters" Tetrahedron Lett. 2008, 49 (46) pp. 6550-6552.

Zajac et al. "Reaction of 2-Butynal Diethyl Acetal with Lithium Aluminum Hydride" J. Org. Chem., 1975 40(4), pp. 530-531.

Astle et al. "Catalysis with Cation-Exchange Resins, Preparation of 1,3 Dioxolanes and 1,3,6-Trioxocanes", Industrial and Engineering Chemistry, Apr. 1954, pp. 787-791.

Singh et al. "Production of Butyl Acetate by Catalytic Distillation. Theoretical and Experimental Studies" Ind. Eng. Chem. Res. 2005, 44, pp. 3042-3052.

Venimadhavan et al. "A Novel Distillate Policy for Batch Reactive Distillation with Application to the Production of Butyl Acetate" Ind. Eng. Chem. Res. 1999, 38, pp. 714-722.

Chadda et al. "Feasibility and Synthesis of Hybrid Reactive Distillation Systems" AIChE Journal, Dec. 2002, vol. 48, No. 12, pp. 2754-2768.

Hibbert et al., J. Am. Chem. Soc. 1924, 46(5), pp. 1283-1290.

Sulzbacher et al., J. Am. Chem. Soc. 1948, 70(8), pp. 2827-2828.

Bronsted and Grove, J. Am. Chem. Soc. 1930, 52(4), pp. 1394-1403.

Van Duzee et al., J. Am. Chem. Soc. 1935, 57, p. 147.

Bonner et al., J. Am. Chem. Soc., Perkins Trans. 1981, pp. 1807-1810.

(56) References Cited

OTHER PUBLICATIONS

Tkachenko et al. "Research in the Field of Furan Acetal Compounds. XII. Features of the Vapor-Phase Hydrogenation of Disubstituted 1,3-Dioxolanes", Chemistry and Technology of Furan Compounds, 1985, pp. 59-64.
Public Dow literature, "Dow Technology Licensing—Meteor™ Ethylene Oxide/Glycol Process Technology," http://www.dow.com/licensing/offer/meteor.htm (downloaded and printed from the internet on Aug. 24, 2011).
Public Shell literature, "Factsheets: OMEGA and ethylene oxide/ethylene glycol technology," http://www.shell.com/home/content/chemicals/aboutshell/media_centre/factsheets/omega/ (downloaded and printed from the internet on Aug. 24, 2011).
Public website at http://globalbiochemna.com/, Global BioChem Technology Group (GBT), Product Information, "About Us, and Glycols Project/Polyol Chemicals" (downloaded and printed from the internet on Aug. 24, 2011).
Public Dow literature, Dow Product Safety Assessment, "Ethylene Glycol Butyl Ether" (EGBE), at http://www.dow.com/productsafety, Product Safety Assessment Finder. (downloaded and printed from the internet on Aug. 24, 2011).
Kul'nevich et al., Khimiya Geterotsiklicheskikh Soyedinenii, No. 8, 1977, pp. 1026-1029.
U.S. Appl. No. 13/168,229, filed Jun. 24, 2011.
U.S. Appl. No. 13/168,274, filed Jun. 24, 2011.
U.S. Appl. No. 13/168,304, filed Jun. 24, 2011.
U.S. Appl. No. 13/168,330, filed Jun. 24, 2011.
U.S. Appl. No. 13/168,361, filed Jun. 24, 2011.
U.S. Appl. No. 13/168,374, filed Jun. 24, 2011.
Luyben, William L., et al.; "Reactive Distillation Design and Control", John Wiley & Sons, 2008, p. 514-517.
Stichlmair, Johann, et al.; "Reactive Distillation Processes"; Chemical Engineering Technology, 22 (1999) 2; pp. 95-103.
USPTO Office Action dated May 21, 2013 for copending U.S. Appl. No. 13/168,374.
USPTO Office Action dated Jul. 1, 2013 for copending U.S. Appl. No. 13/168,229.
USPTO Office Action dated Aug. 15, 2013 for copending U.S. Appl. No. 13/168,330.
USPTO Office Action dated Nov. 1, 2013 for copending U.S. Appl. No. 13/168,274.
USPTO Office Action dated Nov. 1, 2013 for copending U.S. Appl. No. 13/168,304.
USPTO Office Action dated Nov. 4, 2013 for copending U.S. Appl. No. 13/168,361.
USPTO Office Action dated Feb. 26, 2014 for copending U.S. Appl. No. 13/168,229.
USPTO Notice of Allowance dated Dec. 19, 2014 for co-pending U.S. Appl. No. 13/168,374.
USPTO Notice of Allowance dated Feb. 25, 2015 for co-pending U.S. Appl. No. 13/168,274.
USPTO Notice of Allowance dated Jun. 3, 2014 for co-pending U.S. Appl. No. 13/168,374.
USPTO Office Action dated Jun. 4, 2014 for co-pending U.S. Appl. No. 13/168,304.
USPTO Notice of Allowance dated Jun. 17, 2014 for co-pending U.S. Appl. No. 13/168,361.
Copending U.S. Appl. No. 14/307,956, filed Jun. 18, 2014; Damon Ray Billodeaux et al.
USPTO Office Action dated Jul. 2, 2014 for co-pending U.S. Appl. No. 13/168,274.
USPTO Notice of Allowance dated Jul. 7, 2014 for co-pending U.S. Appl. No. 13/168,374.
USPTO Notice of Allowance dated Jul. 9, 2014 for co-pending U.S. Appl. No. 13/168,330.
Copending U.S. Appl. No. 14/337,544, filed Jul. 22, 2014; Daniel Latham Terrill et al.
USPTO Notice of Allowance dated Aug. 4, 2014 for co-pending U.S. Appl. No. 13/168,229.
Copending U.S. Appl. No. 14/459,875, filed Aug. 14, 2014; Damon Ray Billodeaux et al.
English translation of FR 2 906 246 A1, pp. 1-13, Mar. 28, 2008.

\* cited by examiner

US 9,056,313 B2

CATALYSTS FOR THE PRODUCTION OF HYDROXY ETHER HYDROCARBONS BY VAPOR PHASE HYDROGENOLYSIS OF CYCLIC ACETALS AND KETALS

1. FIELD OF THE INVENTION

The invention relates to new catalyst compositions and to the production of hydroxy ether hydrocarbons from the hydrogenolysis of cyclic acetals or cyclic ketals in the vapor phase using certain catalyst compositions.

2. BACKGROUND OF THE INVENTION

Acetals and ketals are readily obtained by the reaction of aldehyde or ketone hydrocarbons and polyhydroxy hydrocarbons by many methods well known in the art. There are many references to the efficient preparation of these materials. It is desirable to prepare 2-alkoxy-ethanol compounds, such as 2-n-butoxyethanol and 2-n-propoxyethanol without the requirement of using ethylene oxide as the reactant. It is also desirable to have a process which is flexible enough to prepare other hydroxy ether compounds without the requirement of using other highly reactive epoxy compounds and similar materials such as propylene oxide, 1,2-epoxybutane, glycidol (2,3-epoxy-1-propanol) and trimethylene oxide. It is also desirable to prepare hydroxy ether compounds in high selectivity without requiring alkylating agents such as alkyl bromides, chlorides and sulfates in their reaction with polyhydroxy compounds in a Williamson ether synthesis with the concurrent production of waste salts.

The classes of compounds known as hydroxy ether hydrocarbons have great value as solvents and dispersants for latex paints and other coatings. They also have value as components of industrial and consumer cleaning solutions and surfactants and raw materials for the preparation of polyurethane materials. The large bulk of this class of compounds that are commercially available are generally known as "E-series" and "P-series" solvents. The "E-series" solvents are prepared by the reaction of ethylene oxide (EO) with corresponding alcohols to form the "E-series" products. Conversely, the "P-series" of solvents are prepared by the reaction of propylene oxide (PO) with corresponding alcohols to form similar materials. This technology has a number of concerns and difficulties. First, ethylene oxide and propylene oxide are hazardous materials. Likewise, the nature of the reaction of an alcohol with highly reactive epoxides generates relatively low selectivity for desirable mono addition of EO or PO to the alcohol resulting in di-, tri and poly-EO or PO addition products in significant amounts. Third, the technology of mono ethylene glycol (MEG) production is moving away from the traditional isolation of ethylene oxide and subsequent reaction with water toward more efficient methods to prepare MEG in higher yield that use other technology, such as ethylene carbonate and direct water quenching of crude EO reactor product. These newer technologies remove a ready source of on-site EO for the production of E-series products. Fourthly, historically, a large capital intensive EO/MEG facility needs to be located in close proximity to the alcohol production facility to be efficient and avoid the risk of having to transport EO over long distances. In the case of "P-series" products, a propylene oxide unit also has to be conveniently located. The traditional preparation of PO involves the co-product formation of precursor materials leading to final products such as styrene and MTBE. Other methods to make PO have been developed, as for example, by the use of expensive hydrogen peroxide. The use of PO to make P-series materials thus has cost concerns.

Dioxolane compounds are characterized by having a five-membered ring with oxygen atoms in the 1 and 3 positions. Other materials based on renewable materials can also be used to prepare acetal compounds by known reactions with aldehydes, including glycerin, 1,3-propanediol and sugar-derived polyols such as mannitol, erythritol, 1,2- and 2,3-butanediol, and the like. In some of these other examples a class of acetal compound having a six-membered ring with oxygen atoms in the 1 and 3 positions known as 1,3-dioxanes can be prepared. Ketals may also be prepared by the reaction of ketone hydrocarbons with the above poly hydroxyl hydrocarbons in a similar manner to that of the preparation of acetals.

Previous work has been disclosed in the literature that discusses the hydrogenolysis of acetals, both cyclic and open to produce ether type hydrocarbons. In the case of 1,3-dioxolane acetal compounds, work has been disclosed that describes the preparation of valuable 2-alkoxy ethanol compounds. This chemical transformation is carried out by the cleavage of the oxygen-carbon bond attached to the carbon in the 2-position of the ring with hydrogen using a noble metal catalyst. The focus of that work has been on the liquid-phase hydrogenolysis of acetals in a solvent that is typically the diol moiety used to prepare the cyclic acetal. The art teaches the importance of having a large excess of this diol solvent present during the hydrogenolysis reaction to prevent the formation of significant amounts of undesired co-product, namely a diether.

U.S. Pat. No. 4,479,017 discusses the desire to generate ether compounds in high selectivity and yield by employing a palladium catalyst on a carbon carrier support in the absence of an added acid promoter compound. U.S. Pat. No. 4,484,009 discloses the product of monoethers of monoethylene glycol by hydrogenolysis of an acetal with a co-catalytic system of a palladium catalyst in combination with an acidic phosphorus promoter compound and ethylene glycol. In both instances, the reactions were conducted in the liquid phase. There remains a need to provide suitable catalyst systems that will generate hydroxy ether hydrocarbons in high selectivity in a vapor phase hydrogenolysis process and in another aspect also without the need for a solvent co-feed material.

3. SUMMARY OF THE INVENTION

There is now provided a process comprising contacting hydrogen with a cyclic compound comprising a cyclic acetal, a cyclic ketal, or a combination thereof in the presence of a catalyst composition comprising an α-aluminum oxide support containing or on which is deposited:
  a. palladium in an amount of up to 1 wt % based on the weight of the catalyst composition, and
  b. up to 1 wt % silicon dioxide based on the weight of the catalyst composition, wherein the BET surface area of the support is less than 30 m2/g.

There is also provided a process comprising contacting hydrogen with a cyclic compound comprising a cyclic acetal, a cyclic ketal, or a combination thereof in the presence of a catalyst composition comprising an γ-aluminum oxide support containing or on which is deposited:
  a. palladium in an amount of up to 1 wt % based on the weight of the catalyst composition, and
  b. up to 1 wt % silicon dioxide based on the weight of the catalyst composition, wherein the BET surface area of the support is within a range of 100 m2/g-350 m2/g.

There is also provided a process comprising contacting hydrogen with a cyclic compound comprising a cyclic acetal, a cyclic ketal, or a combination thereof in the presence of a catalyst composition comprising a zirconium oxide support containing or on which is deposited:
- a. palladium in an amount of up to 1 wt % based on the weight of the catalyst composition, and
- b. up to 1 wt % silicon dioxide based on the weight of the catalyst composition, wherein the BET surface area of the support is less than 0.2 m2/g to 100 m2/g.

There is also provided a catalyst composition comprising an aluminum oxide support containing or on which is deposited:
- (i) palladium in an amount of up to 1 wt %, and
- (ii) a modifier other than lithium acetate comprising an alkali metal, alkaline earth metal, or an organophosphine oxide compound.

There is also provided a catalyst composition comprising a zirconium oxide support containing or on which is deposited:
- (i) palladium in an amount of up to 1 wt %, and
- (ii) a modifier other than lithium acetate comprising an alkali metal, alkaline earth metal, or an organophosphine oxide compound.

The hydrogenolysis reaction of the invention is carried out in the vapor phase to produce hydroxy ether hydrocarbons using any one of the catalysts of the invention.

There is also provided a process comprising contacting hydrogen with a cyclic compound composition comprising cyclic acetal compounds, cyclic ketal compounds, or a combination thereof in the vapor phase and in the presence of any of the catalyst compositions of the invention to produce a hydroxy ether hydrocarbon composition.

There is also provided a process of:
- (a) feeding hydrogen and the cyclic compound composition to a reaction zone within a reaction vessel, and
- (b) conducting a reaction in the reaction zone comprising contacting hydrogen with at least a portion of the cyclic compound composition in the presence of any one of the catalyst compositions of the invention in the reaction zone under reaction zone conditions above the dew point of the cyclic compound composition to produce hydroxy ether hydrocarbons, fed to the reaction zone, and
- (c) withdrawing a product stream from the reaction zone comprising hydroxy ether hydrocarbons, hydrogen, and if present any unreacted cyclic compounds.

There is also now provided a process comprising contacting cyclic compounds in the vapor phase with hydrogen in the presence of any of the catalyst compositions of the invention and in a reaction zone to produce a vapor hydroxy ether hydrocarbon, wherein said cyclic compounds comprise cyclic acetals, cyclic ketals, or a combination thereof.

4. DETAILED DESCRIPTION OF THE INVENTION

As used herein, "cyclic compounds" includes cyclic acetal compounds, cyclic ketal compounds, and combinations thereof. The term "within" includes the end points of a range.

We have surprisingly found that an efficient hydrogenolysis reaction can be carried out to transform cyclic compounds, such as 1,3-dioxolane compounds and 1,3-dioxane classes of compounds, with high selectivity in a vapor phase reaction using catalysts having a combination of features. Improving the selectivity to the production of the desired hydroxy ether mono-hydrocarbon is the criteria of choice because the unconverted compounds can be recycled for conversion to the desired hydroxy ether hydrocarbon, whereas catalysts with high activity but low selectivity are problematic because the cyclic acetals can be converted to by-products which have no possibility of further conversion to desired hydroxy ether mono-hydrocarbons.

We have found that a particular catalyst having a combination of features is highly selective for obtaining the desired hydroxyl ether hydrocarbon product, often in greater than 90% molar selectivity from the converted acetal feed material. The catalyst compositions of the invention and used in the process of the invention are:
- A. catalyst compositions comprising palladium metal supported on aluminum oxide or zirconium oxide having relatively low surface area, a low weight percentage loading of palladium, and a low silica content and
- B. catalyst compositions comprising palladium metal supported on aluminum oxide or zirconium oxide doped with an alkali metal comprising K, Na, Rb, of Cs; an alkaline earth metal, or a triorganophosphine oxide compound.

Silica, carbon, titania, and other supports were not found to provide improved selectivity to the production of hydroxy ether mono-hydrocarbon compounds. The catalyst supports employed in the process are aluminum oxide supports or zirconium oxide supports.

Category A

In this category, the surface area of the supports in the catalyst composition is relatively low. The low surface area of the support is effective to increase the selectivity to obtain the desired hydroxy ether hydrocarbon. The specific surface area most effective will depend on the type of support employed as well as the phase content of the support.

Aluminum oxide has many phases. Suitable phases include alpha, gamma, theta, and delta. For some catalyst compositions of the invention, the phases include the alpha and gamma phases. Each of these phases and their characterization are well known. For example, the α-alumina (alpha) phase has a hexagonal crystal structure which is the most thermodynamically stable form. γ-alumina (gamma) typically has a cubic crystal structure which is also stable at the operating temperatures of the invention. δ-alumina (theta) crystal structure can be characterized as typically having a monoclinic crystal structure, although the crystal structure can vary depending on the calcining temperature. The crystal structure of these forms are known and described in, for example, Kirk Othmer Encyclopedia of Chemical Technology, Volume 2, pages 302-317 (1992).

An α-aluminum oxide support desirably contains more than 95% of its crystal phases in the alpha phase. These ultrapure alpha phase aluminum oxide supports are desirable. Such high purity supports contain at least 97%, or at least 98%, or at least 99% of their phases in the alpha phase. α-aluminum oxide supports that have less than 90% alpha phase content often also contain high amounts of silicon oxide. Alumina supports with high contents of silicon oxide impact the selectivity of the catalyst toward the production of the desired hydroxy ether mono-hydrocarbon. γ-alumina supports have a gamma phase content of at least 95%, or at least 96%, or at least 97%, or at least 98%, or at least 99%. δ-alumina supports have a theta phase content of at least 95%, or at least 96%, or at least 97%, or at least 98%, or at least 99%. Like the alpha phase aluminum oxide supports, silicon oxides such as silicon dioxide reduce the selectivity of the catalyst toward the production of hydroxy ether mono-hydrocarbon compounds.

The BET surface area (determined by the BET method by nitrogen adsorption to DIN 9277) of the aluminum oxide or zirconium oxide support are as follows:
  (i) for α-aluminum oxide supports, less than 30 m2/g, or less than 25 m2/g, or up to 20 m2/g, or up to 15 m2/g, or up to 10 m2/g, or up to 8 m2/g, or up to 6 m2/g, and at least 0.1 m2/g, or at least 0.2 m2/g, or at least 0.5 m2/g. or at least 1 m2/g. or at least 2 m2/g. or at least 3 m2/g. Those with a surface area within a range of 0.1-30 m2/g, or 0.2-30 m2/g, or 0.2-15 m2/g are also suitable and provide good selectivity; and
  (ii) for γ-aluminum oxide, less than 350 m2/g, or less than 300 m2/g, and at least 100 m2/g, or at least 150 m2/g, or at least 200 m2/g. Those with a surface area within a range of 100-350 m2/g, or 150-300 m2/g, or 200-300 m2/g are also suitable and provide good selectivity; and
  (iii) for zirconium oxide supports, up to 100 m2/g, or up to 85 m2/g, or up to 80 m2/g, or up to 75 m2/g, or up to 70 m2/g, or at least 0.2 m2/g, or at least 0.5 m2/g. or at least 1 m2/g, or at least 5 m2/g. or at least 10 m2/g. or at least 15 m2/g. or at least 20 m2/g. or at least 25 m2/g, or at least 30 m2/g. or at least 35 m2/g. Those with a surface area within a range of 1-100 m2/g, or 10-90 m2/g, or 25-70 m2/g are also suitable and provide good selectivity.

Aluminum oxide and zirconium oxide supports with a low weight percentage of palladium loading generally yield catalysts that reduce the formation of byproducts such as diether compounds, ester compounds and other by-products that result from unselective reactions upon the cyclic compound feed and by secondary decomposition of liberated ethylene glycol, a co-product of diether formation. Suitable palladium metal catalyst loadings for the catalyst used in the invention are at least 0.1 wt %, or at least 0.15 wt %, or at least 0.2 wt %, or at least 0.3 wt %, or at least 0.35 wt %, or at least 0.4 wt %, and up to or less than 2.0 wt %, or up to 1.5 wt %, or up to 1.0 wt %, or up to 0.8 wt %, or up to 0.7 wt %, or up to 0.6 wt %, or up to 0.5 wt %. Examples of suitable ranges include 0.1 wt % to 1.0 wt %, or 0.2 wt % to 0.7 wt %, or 0.2 wt % to 0.6 wt %.

Palladium can be loaded onto the supports by any conventional means. Palladium can be added as a metal or as a compound, such as palladium chloride, palladium chloride dihydrate, palladium bromide, palladium iodide, palladium oxide, or an organic palladium salt or complex such as palladium formate, palladium acetate, palladium butyrate and palladium acetylacetonate.

The catalyst compositions of the invention also have a low silicon dioxide content. Supports having a high silicon dioxide content have been found to reduce the selectivity and yield to the product of hydroxy ether mono-hydrocarbon compounds. The supports for the catalysts should have a $SiO_2$ content of no more than 1.0 wt %, or less than 0.5 wt %, or less than 0.3 wt %, or no more than 0.2 wt %, or no more than 0.1 wt %. Those with low contents of silicon dioxide are effective at increasing selectivity. We have found that the desired conversion of a cyclic acetal into a hydroxy ether hydrocarbon may be carried out in a vapor phase hydrogenation by a wide variety of palladium based catalysts.

The catalyst compositions in this Category A are those that have a moderate level of activity, that is, those which do not cause extremely high conversions of the cyclic compound feed across the catalyst. Moderate activity catalysts, that is, those that yield a conversion of the cyclic compound of at least 15%, or at least 20%, and up to 90%, or up to 85% (e.g. 15-90%, or 15-85%, or 20-90%, or 20-85%) generally yield the best selectivity to the desired hydroxy ether hydrocarbon. Low activity catalysts, yielding conversions of the cyclic compound below 20%, are not as desirable due to the inherent inefficiency of requiring a large amount of acetal recovery for recycle and in most cases also having a poor selectivity to the desired hydroxy ether hydrocarbon product based on converted cyclic acetal. The selectivity to the desired hydroxy ether mono-hydrocarbon suffers when the conversion activity of the catalyst is greater than 85%. While catalysts can be used outside these ranges and are within the scope of this invention, those having an activity of conversion of cyclic compounds from 20% to 85% are preferred.

Category B

We have also found that the aluminum oxide (in any phase, including but not limited to α, δ, γ phases) and zirconium oxide supports loaded with palladium and doped with alkali metals (Li, Na, K, Rb, Cs), other than lithium acetate, and alkaline earth metals (Mg, Ca, Sr, Ba) will increase the selectivity of converted acetal into desired products, or at least with a reduction in byproducts that have no utility, with some of the very active but relatively unselective catalyst systems. In these cases, the surface areas of the catalyst supports are not particularly limited and the catalyst loading is also not particularly limited. While these dopants can be used on any of the catalyst compositions in Category A, the effects of these particular dopants are quite marked with the use of highly active catalysts that require improvement in selectivity. Although some of the dopants may actually decrease the activity of the catalyst, this is quite acceptable in the process of the invention because unconverted cyclic compounds can be recycled and subjected to further hydrogenolysis reactions.

Efforts at improving the selectivity of the highly active catalysts were not promising when candidates such as phosphoric acid and lithium acetate were investigated. We have found, however, that the specific dopants mentioned above were effective at improving selectivity of these active catalysts.

The alkali or alkaline earth metal or metals deposited onto the catalyst supports may have an oxidation state of other than zero. The supports may also be doped with alkali metal salts, other than lithium acetate, or alkaline earth metal salts. Suitable salts of alkali metals and alkaline earth metals include organic anions, such as C1-C8 carboxylates and halides such as acetate, chloride and fluoride salts, to increase the selectivity of converted acetal into desired products with some of the very active but relatively unselective catalyst systems. We have found that the anion appears to participate in affecting the selectivity of the metal. For example, the fluoride salt of lithium improves the selectivity of the catalyst while the acetate salt of lithium showed no improvement. In addition to the alkali metals and alkaline earth metals, we have also found that compounds containing triorganophosphine oxide moieties will also modify the selectivity of very active catalyst systems to suppress certain undesired diether co-product formation.

Specific examples of such modifiers used to dope the supports include potassium acetate, sodium acetate, barium acetate, calcium acetate, lithium fluoride, sodium fluoride, sodium chloride, potassium fluoride, potassium chloride, calcium fluoride, calcium chloride, magnesium acetate, magnesium fluoride, magnesium chloride, with potassium acetate, barium acetate, potassium fluoride, and sodium fluoride being preferred.

The dopants can be added to the catalyst supports by any conventional technique. One common technique for the impregnation of catalysts with dopants is the incipient wetness method.

The dopant is dissolved in a suitable solvent, in many cases being deionized water. The catalyst is added to the solution and the amount of solution is sufficient to wet the entire surface of the catalyst without any liquid remaining so as to disperse all the salts onto the support. The solvent is then evaporated leaving the salt dispersed onto the support and in the pores of the support. Vacuum can be applied and the supports agitated to assist migration of the salts into the pores of the support.

The triorganophosphine oxide compound may contain one or two pentavalent phosphorus atoms where each phosphorus atom has a phosphorus-oxygen double bond and each phosphorus atom is bound to hydrocarbon moieties. These can be monotriorganophosphine oxides or bis-triorganophosphine dioxide compounds. The monotriorganophosphine compound can be represented by the general formula. They can be represented by the general formula:

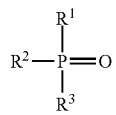

wherein $R^1$, $R^2$, and $R^3$ are independently a branched or unbranched, substituted or unsubstituted alkyl group, aryl group, alicyclic group, or alkaryl group each having from 1 to 20 carbon atoms, or any one of the R groups may be a bridging group having the following general formula:

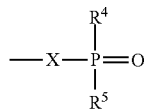

wherein X is a bridging group to form a bis-triorganophosphine dioxide and can be a branched or unbranched, substituted or unsubstituted alkyl group, aryl group, alicyclic group, or alkaryl group each having from 1 to 20 carbon atoms, and $R^4$ and $R^5$ can be selected from any of the groups of $R^1$, $R^2$, or $R^3$ mentioned above.

Examples of phosphine oxides include without limitation butyldiethylphosphine oxide, butyldimethylphosphine oxide, butyldiphenylphosphine oxide, butyldipropylphosphine oxide, decyldiethylphosphine oxide, decyldimethylphosphine oxide, decyldiphenylphosphine oxide, dibutyl (2-methylphenyl)-phosphine oxide, diethyl(3-methylphenyl)-phosphine oxide, ethyldioctylphosphine oxide, ethyldibutylphosphine oxide, ethyldimethylphosphine oxide, ethyldiphenylphosphine oxide, ethyldipropylphosphine oxide, heptyldibutylphosphine oxide, heptyldiethylphosphine oxide, heptyldimethyl phosphine oxide, heptyldipentylphosphine oxide, heptyldiphenylphosphine oxide, hexyldibutylphosphine oxide, hexyldiethylphosphine oxide, hexyldimethyl phosphine oxide, hexyldipentylphosphine oxide, hexyldiphenylphosphine oxide, methylbis(4-methylphenyl)-phosphine oxide, methyldibutylphosphine oxide, methyldidecylphosphine oxide, methyldiethylphosphine oxide, methyldiphenylphosphine oxide, methyldipropylphosphine oxide, octyldimethylphosphine oxide, octyldiphenylphosphine oxide, pentyldibutylphosphine oxide, pentyldiethylphosphine oxide, pentyldimethylphosphine oxide, pentyldiphenylphosphine oxide, phenyldibutylphosphine oxide, phenyldiethylphosphine oxide, phenyldimethylphosphine oxide, phenyldipropylphosphine oxide, propyldibutylphosphine oxide, propyldimethylphosphine oxide, propyldiphenylphosphine oxide, tris(2,6-dimethylphenyl)-phosphine oxide, tris(2-methylphenyl)-phosphine oxide, tris (4-methylphenyl)-phosphine oxide, tris[4-(1,1-dimethylethyl)phenyl]-phosphine oxide, (1-methylethyl)diphenylphosphine oxide, 4-(diphenylmethyl)phenyl]diphenylphosphine oxide, bis(2-methylphenyl)(2-methylpropyl)-phosphine oxide, tributylphosphine oxide, tripropylphosphine oxide, triisopropylphosphine oxide, triethylphosphine oxide, triheptylphosphine oxide, trimethylphosphine oxide, trioctylphosphine oxide, tripentylphosphine oxide, tripropylphosphine oxide, triphenylphosphine oxide, tri-(o-tolyl)phosphine oxide, tri-(p-tolyl)phosphine oxide, tri-(m-tolyl)phosphine oxide, tri-(o-chlorophenyl)phosphine oxide, tri-(p-chlorophenyl)phosphine oxide, tri-(m-chlorophenyl)phosphine oxide, tricyclohexyl phosphine oxide, tribenzylphosphine oxide, dimethyl phosphine oxide, tri-2-methyl propyl phosphine oxide, dimethyldodecylphosphine oxide, 10 dimethyltetradecylphosphine oxide, methylethyltetradecylphosphine oxide, dimethylhexadecylphosphine oxide, dimethyloctadecylphosphine oxide, ethylpropylhexadecylphosphine oxide, diethyldodecylphosphine oxide, diethyltetradecylphosphine oxide, dipropyldodecylphosphine oxide, bis(2-hydroxyethyl)dodecylphosphine oxide, bis-(3-hydroxypropyl)-dodecylphosphine oxide, 20 methyl-2-hydroxypropyltetradecylphosphine oxide, dimethyloleylphosphine oxide, dimethyl-2-hydroxydodecylphosphine oxide, bis(hydroxymethyl)-dodecylphosphine oxide, diethyl-1-hydroxydodecylphosphine oxide, tetraphenyl dimethylene diphosphine dioxide(diphosdioxide), tetraphenyl trimethylene diphosphine dioxide, bis(diphenylphosphino)methane dioxide, 1,2bis(diphenylphosphino)ethane dioxide, 1,3bis(diphenylphosphino)propane dioxide, 1,4bis(diphenylphosphino)butane dioxide; 1,1' bis(diphenylphosphino)ferrocene dioxide, 1,2-bis(di(pentafluorophenyl)phosphino)ethane dioxide, bis(diphenylphosphinoethyl)phenyl phosphine dioxides, or combinations thereof.

One example of such a catalyst composition is a catalyst comprising an aluminum oxide support on which is deposited:
  (i) palladium in an amount of up to 1 wt %, and
  (ii) a modifier, other than lithium acetate, comprising an alkali metal, alkaline earth metal, or a triorganophosphine oxide compound.

Another example of such a catalyst composition is a catalyst comprising a zirconium oxide support containing or on which is deposited:
  (i) palladium in an amount of up to 1 wt %, and
  (ii) a modifier, other than lithium acetate, comprising an alkali metal, alkaline earth metal, or a triorganophosphine oxide compound.

In each of these examples, the type of support and BET surface area of the support may be as described in each of the examples given in Category A. but are not limited to those surface areas. However, the dopants are effective also at improving the selectivity of the catalyst compositions beyond the surface areas described in Category A. The dopants are effective modifiers for highly active catalysts, and those would include compositions having high surface area and high loadings of palladium. Thus, the surface area and palladium loading are not particularly limited in this embodiment. Suitable surface areas of the doped supports are not limited, and can include those having a BET surface area ranging from 1 to 350 m2/g. Suitable loading of palladium ranges from 0.1 wt % up to 5 wt %, or up to 4 wt %, or up to 3 wt %, or up to 2 wt %.

In each of these examples in Category B, the support may contain or have deposited onto the support an alkali metal salt, other than a lithium salt, or an alkaline earth metal salt of C1-C8 carboxylates, chlorides, or fluorides. In each of these examples, the support may contain or have deposited onto the support potassium acetate, sodium acetate, barium acetate, calcium acetate, lithium fluoride, sodium fluoride, sodium chloride, potassium fluoride, potassium chloride, calcium fluoride, calcium chloride, barium chloride, magnesium acetate, magnesium fluoride, magnesium chloride, with potassium acetate, barium acetate, and sodium fluoride being preferred. The catalysts may be additionally doped with other modifiers, including those that do not increase selectivity. It is desirable, however, to avoid the presence of additional dopants which decrease selectivity, retard the activity of the catalyst, do not appreciably increase yield, or are difficult to remove and process.

Any of the catalyst compositions of the invention are useful to provide a selectivity to the production of hydroxy ether mono-hydrocarbons to a level of at least 80%, or at least 82%, or at least 84%, or at least 86%, or at least 88%, or at least 90%, or at least 92%, or at least 94%, or at least 95%. The hydroxy ether mono-hydrocarbons have both (i) at least one ether linkage and (ii) at least one hydroxyl group, and in addition, are those compounds in which the reaction product of cyclic acetal or cyclic ketal with one or more moles of hydrogen has not reacted any further with other cyclic acetals or cyclic ketals or other reaction products of cyclic acetals and cyclic ketals and hydrogen, and has not been subjected to a decrease in its molecular weight due to chain scission. If the cyclic acetal or ketal compound fed to the reaction zone contains 2 or more ether linkages to start, but does not react with any other cyclic acetal or cyclic ketal compounds or any other reaction products of hydrogen with cyclic acetals or cyclic ketals, it is deemed a hydroxy ether mono-hydrocarbon even though more than one ether linkage is present. This is because the reaction product of hydrogen and the cyclic acetal or cyclic ketal having multiple ether linkages has not reacted any further with other cyclic acetals or with any other reaction products of hydrogen and cyclic acetals or cyclic ketals.

The catalysts of the invention also are effective to suppress the formation of diether by-product compounds. It is advantageous to use a catalyst composition that, even though a significant improvement in selectivity is not observed, nevertheless results in the formation of fewer diether by-products. A product stream composition from a vapor phase hydrogenolysis of cyclic hydrocarbons that contains up to 5 wt % of diether compound co-products, or up to 4 wt %, or up to 3 wt %, or up to 2 wt %, or up to 1 wt % are also suitable.

The aluminum oxide supports may be obtained from natural sources or synthesized, such as by calcination of aluminum hydroxide.

The shape of the solid catalysts are not particularly limited but should be of a shape and size and robust enough to resist breaking in a catalyst bed. Spherical and trilobal shapes are shown to be suitable for use in the invention.

The average particle size of the catalysts are not particularly limited. Shapes can be selected to provide efficient mass transfer. Suitable average particle sizes range from 0.1 mm to 8 mm, with 1 mm to 6 mm well suited in the practice of the invention.

The average pore size and pore volume of the supports is not particularly limited. Consideration is given for having pore sizes and pore density to support the palladium metal and provide active sites for the conversion of cyclic compounds to the hydroxy ether mono-hydrocarbon compounds. Typical average pore sizes range from 30 Å to 300 Å, or 60 Å to 200 Å, and typical pore volumes range from 0.2 cc/g to 1.0 cc/g, or 0.3 cc/g to 0.8 cc/g.

The catalysts in each of these examples are useful in the process of the invention.

In the process of the invention, cyclic compounds in a cyclic compound composition are contacted with hydrogen in the vapor phase to produce hydroxy ether hydrocarbons. The cyclic compounds are in the vapor phase at least in the reaction zone and desirably also fed to the reaction zone in the vapor phase. For example, one may hydrogenate the cyclic compounds by:

(a) feeding hydrogen and a cyclic compound composition comprising cyclic compounds, and preferably a cyclic compound vapor composition, to a reaction zone within a reaction vessel, and (b) contacting at least a portion of the cyclic compound composition with hydrogen in the reaction zone under reaction zone conditions above the dew point of the cyclic compound composition fed to the reaction zone to produce hydroxy ether compounds in the reaction zone, and (c) withdrawing a product stream from the reaction zone comprising hydroxy ether hydrocarbons, hydrogen, and if present any unreacted cyclic compounds.

The cyclic compounds can be contacted with hydrogen in a reaction zone over a noble metal catalyst advantageously in the absence of a liquid, such as a solvent like ethylene glycol, in the reaction zone during the hydrogenolysis reaction. Also, advantageously, the noble metal catalyst does not need to be separated from the product stream effluent because the reaction proceeds in the vapor phase over a heterogeneous catalyst bed, preferably a fixed bed.

The cyclic compound composition of the invention contains cyclic compounds. The cyclic compounds that are contacted with hydrogen in the process of the invention are those having a cyclic acetal or ketal moiety. The cyclic acetal moiety produced in the process of the invention has two oxygen atoms single bonded to the same carbon atom in the ring structure. Examples include cyclic compounds having 1,3-dioxolane moieties and dioxane moieties (especially 1,3-dioxane moieties), as well as those having larger rings with oxygen atoms in the 1,3 position.

In one embodiment, the cyclic compound(s) may be represented by the general formula:

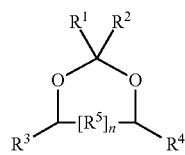

wherein $R^1$, $R^2$, $R^3$, and $R^4$ are independently H; an branched or un-branched $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cycloalkyl, or a $C_3$-$C_{50}$ carboxylate ester; and wherein the alkyl, alkenyl, aryl, and cycloalkyl groups of $R^1$, $R^2$, $R^3$, and $R^4$ are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol;

and any one or both of $R^3$ and $R^4$ are optionally independently a hydroxyl, halogen, dialkylamino, amine, aldehyde, ketone, carboxylic acid, ester, ether, alkynyl, dialkylamide, anhydride, carbonate, epoxide, lactone, lactam, phosphine, silyl, thioether, thiol, or phenol;

and wherein $R^1$ and $R^2$ are not both H;

and $R^1$ and $R^2$ optionally together form a cycloalkyl having 3-12 carbon atoms;

and wherein $R^5$ is branched or unbranched, substituted or unsubstituted, divalent alkyl or divalent alkenyl group each having 1 to 8 carbon atoms and optionally containing 1, 2, or 3 oxygen atoms in the alkyl or alkenyl group;

and wherein n is an integer selected from 0 or 1.

$R^1$, $R^2$, $R^3$, and $R^4$ may independently be H, or a branched or un-branched $C_1$-$C_6$ alkyl group. Or, $R^1$, $R^2$, $R^3$, and $R^4$ may independently be H, or a branched or un-branched $C_1$-$C_4$ alkyl group. $R^1$ may be a branched or unbranched $C_1$-$C_6$ alkyl group while $R^2$ is a hydrogen atom.

$R^5$ may be a branched or unbranched divalent alkyl group having 1 to 6, or 1 to 4, or 1 to 3, or 1 to 2 carbon atoms.

Examples of cyclic acetals include 2-propyl-1,3-dioxolane, 2-propyl-1,3-dioxane, 2-ethyl-1,3-dioxolane, 2-ethyl-1,3-dioxane, 2-methyl-1,3-dioxolane, 2-methyl-1,3-dioxane, 2-propyl-4-methyl-1,3-dioxane, 5,5-dimethyl-2-propyl-1,3-dioxane, 5,5-dimethyl-2-ethyl-1,3-dioxane, 4-hydroxymethyl-2-propyl-1,3-dioxolane, 4-hydroxymethyl-2-propyl-1,3-dioxane, 2-ethyl-1,3-dioxepane, 2-ethyl-1,3,6-trioxocane.

As to substituents, in one embodiment, $R^3$ or $R^4$ is a hydroxyl group.

In the case one desires to use a cyclic acetal compound as a starting material, one of $R^1$ or $R^2$ is a hydrogen atom. $R^1$ and $R^2$ may independently be H, or a branched or un-branched $C_1$-$C_6$ alkyl group. Or, $R^1$ and $R^2$ may independently be H, or a branched or un-branched $C_1$-$C_4$ alkyl group. $R^1$ may be a branched or unbranched $C_1$-$C_6$ alkyl group while $R^2$ is a hydrogen atom. Particularly useful cyclic acetals for this invention leading to useful materials of commerce include 1,3-dioxolanes having $R^1$ being an alkyl group that can lead to "E-series" type solvents. Likewise, 1,3-dioxolanes having $R^1$ being an alkyl group and $R^3$ being a methyl group can lead to "P-series" type solvents.

In the case one desires to start with a cyclic ketal compound as the starting material, then neither $R^1$ nor $R^2$ are hydrogen atoms. $R^1$ and $R^2$ may independently be a branched or un-branched $C_1$-$C_6$ alkyl group. Or, $R^1$ and $R^2$ may independently be a branched or un-branched $C_1$-$C_4$ alkyl group. Other potentially useful acetals that make use of 1,3-propylene glycol and glycerin in their preparation would include 1,3-dioxane acetals having $R^1$ being an alkyl group and 1,3-dioxane acetals having $R^1$ being an alkyl group and $R^4$ being a hydroxyl group. A variation of the glycerin acetals that have potentially useful derivatives would be 1,3-dioxolane acetals having $R^1$ being an alkyl group and $R^3$ being a hydroxymethyl group.

Examples of cyclic acetals that have 1,3-dioxolane moieties include 2-propyl-1,3-dioxolane, 2-propyl-1,3-dioxolane, 2-ethyl-1,3-dioxolane, 2-methyl-1,3-dioxolane, 4-hydroxymethyl-2-propyl-1,3-dioxolane.

Examples of cyclic acetals that have 1,3-dioxane moieties include 2-propyl-1,3-dioxane, 2-ethyl-1,3-dioxane, 2-methyl-1,3-dioxane, 2-propyl-4-methyl-1,3-dioxane, 5,5-dimethyl-2-propyl-1,3-dioxane, 5,5-dimethyl-2-ethyl-1,3-dioxane, and 4-hydroxymethyl-2-propyl-1,3-dioxane.

Examples of cyclic ketals that can be utilized in the present invention include, but are not limited to, 2,2-dimethyl-1,3-dioxolane, 2,2-dimethyl-1,3-dioxane, 2,2,4-trimethyl-1,3-dioxolane, 2,2-dimethyl-1,3-dioxepane, 2,2-dimethyl-1,3,6-trioxocane, 4-methanol-2,2-dimethyl-1,3-dioxolane, 2,2-dimethyl-1,3-dioxan-5-ol, 2,2,5,5-tetramethyl-1,3-dioxane, 2-ethyl-2-methyl-1,3-dioxolane, 2-ethyl-2-methyl-1,3-dioxane, 2-ethyl-2,4-dimethyl-1,3-dioxane, 2-ethyl-2-methyl-1,3-dioxepane, 2-ethyl-2-methyl-1,3,6-trioxocane, 2-ethyl-2,5,5-trimethyl-1,3-dioxane, 4-methanol-2-ethyl-2-methyl-1,3-dioxolane, 2-ethyl-2-methyl-1,3-dioxan-5-ol, 2-methyl-2-propyl-1,3-dioxolane, 2-methyl-2-propyl-1,3-dioxane, 2,4-dimethyl-2-propyl-1,3-dioxane, 2-methyl-2-propyl-1,3-dioxepane, 2-methyl-2-propyl-1,3,6-trioxocane, 2,5,5-trimethyl-2-propyl-1,3-dioxane, 4-methanol-2-methyl-2-propyl-1,3-dioxolane, 2-methyl-2-propyl-1,3-dioxan-5-ol, 2-methyl-2-pentyl-1,3-dioxolane, 2-methyl-2-pentyl-1,3-dioxane, 2,4-dimethyl-2-pentyl-1,3-dioxane, 2-methyl-2-pentyl-1,3-dioxepane, 2-methyl-2-pentyl-1,3,6-trioxocane, 2,5,5-trimethyl-2-pentyl-1,3-dioxane, 4-methanol-2-methyl-2-pentyl-1,3-dioxolane, and 2-methyl-2-pentyl-1,3-dioxan-5-ol.

The cyclic acetals and ketals are prepared by reacting a polyhydroxyl compound with a carbonyl functional compound that is either an aldehyde or a ketone, in the present of an acid catalyst.

The cyclic acetals and ketals are prepared by reacting a polyhydroxyl compound with a carbonyl functional compound that is either an aldehyde or a ketone, in the present of an acid catalyst.

The polyhydroxyl compounds have at least two hydroxyl (—OH) functionalities. The polyhydroxyl compounds may contain ether or ester linkages in the longest carbon chain.

Suitable polyhydroxyl compounds for the present invention include, but are not limited to ethylene glycol, 1,2-propanediol, 1,3-propanediol, 1,4-butanediol, 1,3-butanediol, 1,2-butanediol, 1,2-pentanediol, 2,4-pentanediol, 2,2-dimethyl-1,3-propanediol, diethyleneglycol, and triethyleneglycol, glycerin, trimethylolpropane, xylitol, arabitol, 1,2- or 1,3cyclopentanediol, 1,2- or 1,3-cyclohexanediol, and 2,3-norbornanediol.

The carbonyl compounds contain at least one carbonyl functionality. In the present invention, any carbonyl compound may be used.

For example, the carbonyl compound is represented by the formula:

in which $R^1$ and $R^2$ are independently H, $C_1$-$C_{50}$ alkyl, $C_2$-$C_{50}$ alkenyl, aryl-$C_1$-$C_{50}$ alkyl, aryl-$C_2$-$C_{50}$ alkenyl-, or $C_3$-$C_{12}$ cycloalkyl, and wherein the alkyl, alkenyl, aryl, and cycloalkyl groups of $R^1$ are optionally saturated or unsaturated, and branched or unbranched or substituted or unsubstituted with 1, 2, or 3 groups comprising —OH, halogen, dialkylamino, $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, aryl, phenol, or combinations thereof. $R^1$ and $R^2$ optionally together form a cycloalkyl having 3-12 carbon atoms;

When one of $R^1$ and $R^2$ is hydrogen, the carbonyl compound is an aldehyde compound. The aldehyde compound may have, if desired, at least one aldehyde functional group wherein the aldehyde carbon atom is bonded to a (i) branched or unbranched $C_1$-$C_9$ alkyl group or (ii) an aryl or alicyclic group which is optionally substituted with a branched or unbranched $C_1$-$C_9$ alkyl group.

Examples of aldehyde compounds include, but are not limited to, formaldehyde, benzaldehyde, acetaldehyde, propionaldehyde, butyraldehyde, isobutyraldehyde, pentaldehyde, 2-methylbutyraldehyde, 3-methylbutyraldehyde, n-pentanal, isopentanol, hexyldehyde, heptaldehyde, 2-ethylhexaldehyde, octanal, nonanal, n-decanal, 2-methylundecanal, lauryl aldehyde, myristyl aldehyde, cetyl aldehyde, stearyl aldehyde, behenyl aldehyde, glutaraldehyde, acrolein, crotonaldehyde, oleyl aldehyde, linoleyl aldehyde, linolenyl aldehyde, erucyl aldehyde, cinnamaldehyde, 1,3-cyclohexanedicarboxaldehyde, 1,4-cyclohexanedicarboxaldehyde, and combinations thereof.

When neither $R^1$ nor $R^2$ is hydrogen, the carbonyl compound is a ketone. Examples of suitable ketone compounds include, but are not limited to, acetone, methyl isobutyl ketone (2-butanone), methyl ethyl ketone, methyl propyl ketone (2-pentanone), methyl isopropyl ketone (3-methyl-2-butanone), methyl isobutyl ketone (4-methyl-2-pentanone), 2-hexanone, cyclohexanone, 2-heptanone (methyl amyl ketone), 4-heptanone, and 2-octanone.

The starting feed materials used in the process of the invention comprise cyclic acetal compounds or cyclic ketal compound or combinations thereof. The process of the invention is a vapor phase reaction conducted at an elevated pressure. Therefore, the feed materials selected should be sufficiently volatile to enter the reaction vessel in a gaseous state as a gaseous feed stream. Accordingly, the feed materials must have a pure liquid vapor pressure of at least 1 mm Hg (0.133 kPa) (at the reaction temperature). To obtain better reaction rates, it is desired to select a feed material that has a vapor pressure in excess of 10 mm Hg (1.33 kPa).

For example, feed material compounds with relatively high boiling points like a cyclic acetal or ketal compound can be selected with high boiling points (at 1 atm) in excess of 200° C. or even at least 250° C. (523 degrees K) because those same compounds may have practical vapor pressures of in excess of 50 mm Hg or at least 70 mm Hg (9.33 kPa) at typical hydrogenolysis reaction temperatures (at least 150° C., or at least 180° C. or at least 190° C. or at least 200° C.) in the reaction vessel.

The process has the ability to be operated at a wide range of reaction temperature conditions. Suitable reaction temperatures (reactor set points) range from at least 100° C., or at least 130° C., or at least 150° C., or at least 170° C., or at least 180° C., or at least 190° C., or at least 200° C., or at least 210° C., or at least 220° C., and up to 300° C., or up to 275° C., or up to 250° C., or up to 240° C., or up to 230° C., or up to 220° C., or up to 210° C., or up to 200° C.

The favored temperature range for the practice of the invention is at least 150° C. because reaction rates increase at higher temperatures and up to about 250° C. Temperatures in excess of 250° C. start to suffer from excessive side product reactions. Suitable ranges include 190° to 250° C., or 200° to 230° C.

We have found that the efficiency of the process is increased if the operating reaction conditions are at temperatures above the dew point of the cyclic compound composition in the gaseous feed stream at reaction pressure. In another embodiment, the operating reaction conditions are at a temperature above the dew point of both the cyclic compound composition and the reaction products of the cyclic acetals in the gaseous product stream.

Dew point is defined as the temperature and pressure at which liquid condensation begins to take place for a gaseous mixture having a condensable material. See Dictionary of Scientific and Technical Terms published by McGraw-Hill, Fifth Edition, 1994. In practice, dew point is controlled by a combination of factors. The first factor is the actual vapor pressure of a pure liquid as a function of temperature. Increasing temperature increases the vapor pressure of a pure liquid thereby making it less likely to condense at higher temperature. Cyclic acetals and ketals behave in this manner. Lowering the temperature also lowers the vapor pressure of the liquid. Thus, operating the reaction at lower temperatures will require lowering the pressure in the reaction vessel to prevent the cyclic acetals from dropping below their dew point. It is desirable to conduct the hydrogenolysis at elevated temperatures in order to keep materials from condensing into a liquid phase at reaction conditions.

The second factor that keeps the cyclic compounds in the gaseous state and prevents them from dropping below their dew points is to keep the reactor absolute pressure low enough to keep the actual partial pressure of the component cyclic acetals above the dew point in the gaseous feed. The partial pressure of the cyclic acetals is related to the vapor pressure of the pure compounds at reaction temperature. Partial pressure (PP) of a given component "b" is defined: P(absolute)×(mole fraction of b in the mixture). Mole fraction is the portion of moles of the component in the total moles of a mixture. The partial vapor pressures of organic materials in this invention at reaction pressure and temperature must remain below the vapor pressure of the pure materials at that reaction temperature to avoid condensation. In essence, lowering reactor absolute pressure of a given mole fraction of reactant cyclic acetal in the feed will thereby lower the partial pressure of the reactant cyclic acetal. The vapor pressures of pure materials may be obtained by normal calculations with established physical constants or obtained from vapor pressure tables. For example one such method of vapor pressure calculation for the pure compound 2-n-propyl-1,3-dioxolane (PDX) would be: vapor pressure of PDX in mm Hg=10**((−0.2185×(A/K)+B) where A=10183.9; K=Temperature of the PDX in degrees Kelvin; and B=+8.363358. Thus the vapor pressure of pure PDX would be about 4560 mm Hg (607.95 kPa) at 200 degrees Celsius (473 degrees K).

Without being bound to a theory, not having liquid condensation on the surface of the supported noble metal catalyst facilitates the transfer of gaseous hydrogen into the catalytic cycle. Indeed, we have found improvement in catalyst performance when progressively lower partial pressures of organic reactants are used at a given reactor temperature and pressure.

The hydrogenolysis reaction uses hydrogen as both a gaseous feed medium and reactant in this invention. A hydrogenolysis reaction uses hydrogen to cleave the carbon-oxygen bond of either the 1,2 carbon-oxygen bond or the 2,3-carbon-oxygen bond by means of the supported noble metal catalyst. The purity of the hydrogen being fed to the reactor is high enough to effect the desired reaction and not contain significant amounts of impurities that could act as poisons or inhibitors. Inert hydrocarbons such as methane, ethane, propane and butane are managed by normal gas purging methods to keep the desired partial pressure of reactant hydrogen present in the reactor. For certain impurities such as carbon monoxide, methods such as nickel methanation catalyst beds and the like can be used to convert this poison into an inert methane impurity and thereby control the concentration of CO in the reactor feed stream.

The amount of hydrogen fed in the continuous process can be that amount sufficient to enhance selectivity to the hydroxy ether mono-hydrocarbon. The amount of hydrogen used will vary depending on the reaction conditions and type of cyclic compound used as the substrate, but generally, a molar ratio of hydrogen to cyclic compound of at least 5:1 is suitable. Other examples of molar ratios of hydrogen to cyclic compounds include at least 10:1, or at least 50:1, or at least 100:1, or at least 150:1, or at least 170:1, or at least 190:1, or at least 200:1, or at least 250:1, and can be as high as desired. It is desirable to adjust the molar ratio to increase selectivity. The selectivity is improved with the catalyst compositions of the invention when the molar ratio exceeds 100:1, or is at least 125:1, or is at least 150:1.

The reactor pressures used may be from one atmosphere absolute (or 0 psig or 0 kPa gauge), or from at least 5 atm, or from at least 8 atm, or from at least 10 atm, or from at least 12 atm, or from at least 13 atm, or from at least 15 atm, or from at least 20 atm (about 300 psig), or at least 28 atm (400 psig) and up to 141 atmospheres (2000 psig), or up to 105 atmospheres (1500 psig), or up to 88 atmospheres (1250 psig), or up to 69 atmospheres (or 1000 psig, or 6895 kPa) or up to 51 atmospheres (or 750 psig, or 5171 kPa gauge), or), or up to 45 atm, or up to 40 atm, or up to 35 atm, or up to 30 atm, or up to 27 atm, or up to 25 atm, or up to 10 atm. Suitable reactor pressures can range from at least 10 atm, or at least 13 atm, and up to 141 atm, or up to 105 atm, or up to 88 atm. One example of a suitable range is from 13 atm to 141 atm (200 to 2000 psig), or atm (300 psig to 88 atm (1250 psig), for many practical operations.

The reactor design is not crucial for the operation of this invention. The reactor should be designed to permit a gaseous mixture of hydrogen and the cyclic compounds to pass over the supported noble metal catalyst and exit the reactor zone with the desired hydroxy ether hydrocarbon as a gaseous product mixture. Convenient designs include plug flow reactors such as long tubular designs and multi-tube short path designs. Other reactors known as "pancake" reactors have a wide continuous catalyst bed that is of a relatively short path. The process can also be conducted in exotic designs such as spinning basket or Berty type reactors can be used. In all reactor designs, however, the catalyst bed should remain at a temperature above the dew point of the reactants and products at the reactor conditions used. Additionally, the design of the reactor feed system should be designed to keep the feed composition compositionally balanced so that the partial pressures of the cyclic compounds fed to the reactor remain above the dew points of the cyclic compounds under the operating reactor conditions. This may be easily achieved by use of vapor liquid equilibrium feed chambers or by controlling the rates of liquid and hydrogen feed rate to the reactor via a mixing chamber to assure complete vaporization of the cyclic compounds at the reactor conditions prior to contact with the hydrogenolysis catalyst bed and to maintain the cyclic compounds at the proper feed partial pressure.

No polyhydroxyl hydrocarbon co-solvent feed, such as ethylene glycol, is required in a vapor phase hydrogenolysis conversion process. Thus, an advantage of the current process is conducting a conversion of cyclic compounds to their corresponding hydroxy ether hydrocarbon reaction products in the absence of a liquid solvent feed, such as ethylene glycol, at high selectivities.

The conversion rates from the cyclic compounds to any and all converted reaction products can be at least 35%, or at least 75%, or at least 90%, or at least 92%, or at least 94%, or at least 95%.

The product stream is withdrawn from the reaction zone. The product stream contains a hydroxy ether reaction product of the cyclic compound(s) with hydrogen. The reaction zone reaction conditions can be set to ensure that the hydroxy ether reaction product remains above its dew point. The reaction conditions can also be set within the reaction zone to ensure that the product stream withdrawn from the reaction zone remains above its dew point and is a vapor. When the product stream is withdrawn from the reaction zone as a vapor, the product stream will also contain other types of compounds in minor amounts, such as by-products, hydrogen gas, and unreacted cyclic acetal or ketal compounds.

In the vapor phase hydrogenolysis of the cyclic compounds over a heterogeneous supported noble metal catalyst, the noble metal catalyst is not withdrawn in the product stream. The product stream withdrawn advantageously does not contain any appreciable quantities of the noble metal catalyst that have to be separated from the desired hydroxy ether hydrocarbon. In one embodiment of the invention in the product stream withdrawn from the reaction zone contains less than 500 ppmw of the metal catalyst used in the reaction zone, or less than 100 ppmw, or less than 50 ppmw, or less than 25 ppmw, or less than 10 ppmw, or less than 5 ppmw, or less than 2 ppmw, based on the weight of all ingredients fed to the reaction zone.

Suitable hydroxy ether hydrocarbons are the reaction products of the cyclic compounds with hydrogen gas resulting in a hydrocarbon with at least one ether linkage and at least one primary hydroxyl group. The hydroxy ether hydrocarbons may contain secondary hydroxyl groups, and additional ether linkages. In one embodiment, the hydroxy ether hydrocarbons are represented by the general formula:

$$R^6OR^7OH$$

wherein $R^6$ is a branched or un-branched $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cycloalkyl, or a $C_3$-$C_{50}$ carboxylate ester; and wherein the alkyl, alkenyl, aryl, and cycloalkyl groups of $R^6$ optionally contain 1, 2, or 3 oxygen atoms in the alkyl, cycloalkyl, or alkenyl group and are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol.

In the case that the cyclic compound starting material is a cyclic ketal, then $R^6$ branched at least at the carbon adjacent the ether linkage in the general formula above. The branch can be selected from the same groups as $R^6$.

$R^7$ is a branched or un-branched divalent $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cycloalkyl, or a $C_3$-$C_{50}$ carboxylate ester; and wherein the divalent alkyl, alkenyl, aryl, and cycloalkyl groups of $R^7$ optionally contain 1, 2, or 3 oxygen atoms in the divalent alkyl, cycloalkyl, or alkenyl group and are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol.

The $R^6$ group of the general formula may be a branched or un-branched $C_1$-$C_{12}$ alkyl or aryl-$C_1$-$C_{12}$ alkyl; optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol.

The $R^7$ group of the general formula may be a divalent branched or un-branched $C_1$-$C_{12}$ alkyl or a $C_2$-$C_{12}$ alkenyl; and wherein the divalent alkyl or alkenyl groups of $R^7$ optionally contain 1, 2, or 3 oxygen atoms in the divalent alkyl or alkenyl groups and are optionally substituted with 1, 2, or 3 groups independently selected from —OH or halogen.

In each case above, the alkyl groups may have from 1-8 carbon atoms, or 1-6 carbon atoms, or 1-4 carbon atoms, and the alkenyl groups may have from 2-8 carbon atoms, or 2-6 carbon atoms, or 2-4 carbon atoms.

Examples of the types of hydroxy ether hydrocarbons that are made by the process of the invention include ethylene glycol propyl ether, ethylene glycol butyl ether, ethylene glycol 2-ethylhexyl ether, diethylene glycol methyl ether, diethylene glycol ethyl ether, diethylene glycol propyl ether, diethylene glycol butyl ether, propylene glycol methyl ether, ether, 3-butoxy-1,2-propanediol, 2-butoxy-1,3-propanediol, 2-isopropoxyethanol, isopropoxy-2-propanol, 3-isopropoxypropanol, 2-(3-methyl-2-butoxy)ethanol, 3-(3-methylbutan-2-yloxy)propanol, 2-(4-methylpentan-2-yloxy)ethanol, 3-(4-methylpentan-2-yloxy)propanol, 3-(4-methylpentan-2-yloxy)-1,2-propanediol, 2-(4-methylpentan-2-yloxy)-1,3-propanediol, 2-(pentan-2-yloxy)ethanol, 3-(pentan-2-yloxy)-propanol, 2-(pentan-2-yloxy)-1,3-propanediol, 3-(pentan-2-yloxy)-1,2-propanediol, 2-(methyl-hexyloxy) ethanol, 3-(methyl-hexyloxy)-propanol, 2-(methyl-hexyloxy)-1,3-propanediol, 3-(methyl-hexyloxy)-1,2-propanediol.

The hydroxy ether hydrocarbons have a wide variety of uses. They can be used as solvents, coalescents and plasticizers in all-purpose cleaners, architectural coatings, automotive coatings, cleaners for ink processes, coalescents for latex paints, coatings for plastics, floor cleaners, solvents for removing photoresists in semiconductor wafers, glass cleaners, household cleaners, industrial cleaners, industrial coatings, and metal brighteners and cleaners. They can be used a solvents for a large variety of coatings resin types, including alkyd, phenolic, maleic, epoxy, and nitrocellulose resins. They are also useful as retarder solvent for lacquers, improving gloss and flow-out. Some of the hydroxy ether hydrocarbons can also be used in amine-solubilized, water-dilutable coatings because of their high flash point, complete water solubility, slow evaporation rate, low surface tension, and high coupling efficiency. As coalescents, they improve film integrity in both architectural and industrial maintenance latex paints.

The desired hydroxy ether hydrocarbon can be readily separated from the product stream. One particularly useful method is to cool the gaseous reactor product stream to below the dew point of the reaction products and unreacted cyclic compounds to form a liquid product and from which a gaseous stream comprised primarily of hydrogen gas (greater than 70 vol. %) is easily separated. When the cooling is carried out at reactor pressure, very little energy is required to re-circulate the un-reacted hydrogen back as a feedstock reactant stream to the reactor vessel. The condensed liquid products may then be recovered and purified by known methods, such as distillation, extraction, crystallization and the like to obtain the desired product. Similarly, a liquid scrubber may be employed to recover condensable liquid products from the gaseous reactor effluent. These and other known methods of product recovery may be used in combination with the hydrogenolysis process of this invention.

The process of the invention is carried out batchwise or continuously, preferably continuously.

WORKING EXAMPLES

The liquid feed part of the hydrogenolysis unit consists of a 100 mm graduated burette feed tank for the acetal feed. This is connected to a flow programmable high pressure lab scale ball and check feed pump (Eldex ReciPro Optos Series Model 1). All equipment under pressure is constructed of 316 stainless steel tubing or fittings. The discharge of the pump leads to ⅛ inch diameter (3.2 mm) tubing that is connected to a fitting on the top of the reactor. This fitting is further connected to a ⅛ inch diameter (3.2 mm) tubing section that leads to a vaporization section prior to the catalyst bed. Hydrogen feed is supplied from high pressure cylinders of zero grade hydrogen via a high pressure regulator to a lab scale Brooks mass flow controller. Nitrogen feed, used for purging and other inert gas needs, is fed by a similar design from a high pressure cylinder via a gas regulator through another dedicated Brooks mass flow controller for inert gas flow. The discharges from these two mass flow controllers are connected by a manifold to a ¼ inch diameter (6.35 mm) tubing feed line that is connected to the top of the reactor. The hydrogen or inert gas feeds enter the reactor by an annulus around the ⅛ inch diameter liquid feed line and mix with the liquid above the vaporization section in the reactor.

The reactor is a 24" (70 cm) long×½" diameter (12.7 mm) section of high pressure tubing held in a vertical arrangement. The top part of the reactor consists of a stainless steel Swagelok cross with the appropriate fittings required to permit liquid feed to the reactor via the ⅛ inch diameter (3.2 mm) tubing, to permit hydrogen or other gas feed to the reactor via ¼ inch (6.35 mm) tubing and to connect to a pressure gage and a safety pressure relief device. The top portion of the reactor consists of a bed 4" (10 cm) deep of fused alumina beads 2-3 mm in diameter that are used for the vaporization of the liquid feed in contact with the gaseous hydrogen feed. The reactor is jacketed with a 1" diameter brass round stock bored through the linear axis to receive the ½ stainless steel tubing. Four thermocouple wells were drilled into the brass at a 45 degree angle to receive thermocouples at the top and bottom of the vaporizer section and at the top 1-2" inches of the bed and at the bottom of the catalyst bed. A spacer of pyrex wool packing is used to separate the vaporizer section from the catalyst section of the bed that is downstream from the vaporizer. The lab unit normally uses 20 cubic centimeters of the hydrogenolysis catalyst used in this invention. The depth of the bed is approximately 10 inches (25 cm) deep. The bed is held in place by another spacer of pyrex wool packing and a support of ¼ inch (6.35 mm) diameter tubing to hold it in place. A second thermocouple is attached with similar insulation to the outer skin of the reactor tubing about 2 thirds of the depth of the catalyst bed towards the bottom and is used both as a control point and measure of the reactor temperature. The reactor tubing is placed inside a "clam shell" heater that is electrically heated and controlled by the temperature recorded by the thermocouple located near the bottom of the catalyst bed.

The ½ inch (12.7 mm) tubing of the bottom of the reactor is connected by appropriate Swagelok fittings to a 1" 316 stainless steel "T". This "T" is filled with ⅛" stainless steel Penn State packing material as a coalescer and is cooled by way of a circulating bath to copper tubing on the outside of the "T". This "T" is a high pressure vapor/liquid (V/L) separator where liquid product is condensed for recovery. The bottom of the "T" has a needle valve connected to a small section of ⅛" diameter (3.2 mm) tubing where the collected liquid product is drained periodically. The side fitting of the "T" consists of ½ (12.7 mm) tubing that provides an exit for the uncondensed hydrogen and other gases. The side fitting also has a thermocouple in it to measure the inside temperature of the "T". The gases leaving the side tubing of the "T" are then directed upwards to a back pressure regulator that controls the pressure of the reactor. Gases leaving downstream from the back pressure regulator are at ambient pressure and proceed to a dry ice trap to collect any material that may not have been removed in the V/L separator.

Example 1

Vapor Phase Hydrogenation Using Evonik Degussa 0.5% Pd/Alumina

The liquid feed tank of the hydrogenolysis unit was filled with 2-n-propyl-1,3-dioxolane (PDX). The reactor had been charged with 20 cc (14.27 grams) of Evonik Degussa 0.5% Pd/1/16" alumina sphere catalyst. The hydrogen flow was set at 2960 sccm and the back pressure regulator was set to 300 psig (2068 kPa). The catalyst bed (skin) temperature target was set at 210 degrees Celsius (483 degrees K). After reaching 210 degrees (483 degrees K), the reactor was permitted to equilibrate at 210 degrees Celsius (483 degrees K) for fifteen minutes. After that period, the PDX pump was started with a target feed rate of 0.12 ml/minute. Liquid product samples were collected hourly as was operating data. The samples were weighed and analyzed by gas chromatographic analysis on Agilent Technologies 6890 series machine having a thermal conductivity detector. The column used was a 30 m J & W 125-3232 DB-FFAP capillary column. A 6 minute hold was used at 40 degrees C. followed by a 10 deg/min heat up rate to a final temperature of 220 deg C. and a final 5 minute hold at 220 deg. C. Response factors were used in normal standard practice to obtain the weights of the different components.

The last four hours of samples and feed level drop were used to perform calculations on the conversion of PDX into the desired product 2-n-butoxyethanol. A total of 26.3 ml of PDX (24.67 grams) was fed during the last four hours. A total of 12.43 grams of PDX was recovered, 11.78 grams of 2-n-butoxyethanol (EB), 0.13 grams of 1,2-di-n-butoxyethane (DBE), 0.05 grams of methyl-n-butylether (MBE), 0.19 grams of ethyl n-butyrate (EtButyr), 0.03 grams of ethylene glycol (EG) and 0.08 grams of other organic materials were recovered. The conversion of the PDX was 49% with a selectivity of consumed PDX to 2-n-butoxyethanol of 96.4%. The H2/PDX feed mole ratio of this run was 161/1 with the PDX partial pressure in the reactor at 100.4 mm Hg. The specific production rate of the desired 2-n-butoxyethanol was 9.20 lb/cu-ft-hr (147.3 grams/liter-hr).

The table of runs below used the same charge of catalyst, namely a 20 cc sample of Evonik Degussa 0.5% Pd/1/16" diameter alumina spheres in the above described unit and demonstrates the effect of better selectivity to desired 2-n-butoxyethanol product with progressively lower partial pressures of PDX in the reactor feed brought about by having higher H2/PDX feed mole ratios.

TABLE 1

| Run | T Deg Celsius (K) | Grams PDX/hr | H2/PDX mole ratio | Partial Press PDX mm Hg (kPa) | % PDX Conversion | Grams last 4 hrs EB | Grams last 4 hrs DBE | Grams last 4 hrs MBE | Grams last 4 hrs EtButyr | % Selectivity to EB on converted PDX |
|---|---|---|---|---|---|---|---|---|---|---|
| 1 | 210 (483) | 13.45 | 18.5/1 | 836 (111) | 25 | 9.05 | 0.0 | 0.19 | 1.35 | 83.2 |
| 2 | 210 (483) | 13.45 | 54.4/1 | 294 (39) | 24 | 9.81 | 0.0 | 0.05 | 0.64 | 91.1 |
| 3 | 210 (483) | 13.45 | 92/1 | 175 (23) | 32 | 11.71 | 0.0 | 0.036 | 0.52 | 93.8 |
| 4 | 220 (493) | 13.45 | 91.7/1 | 176 (23) | 44 | 19.00 | 0.14 | 0.072 | 0.72 | 93.6 |
| 5 | 210 (483) | 6.73 | 68.2/1 | 235 (31) | 53 | 11.08 | 0.19 | 0.064 | 0.31 | 94.4 |
| 6 | 210 (483) | 6.73 | 161/1 | 100 (13) | 49 | 11.78 | 0.13 | 0.05 | 0.19 | 96.4 |

All reactions carried out at 300 psig.
PDX = 2-n-propyl-1,3-dioxolane; EB = 2-n-butoxyethanol; MBE = methyl-n-butylether; EtButyr = ethyl n-butyrate; DBE = 1,2-di-n-butoxyethane.

Example 2

Conversion Rates

We have found that the more desirable catalysts are those which are not of high activity, that is, those which do not cause extremely high conversions of the cyclic acetal feed across the catalyst bed. Table 2 below lists the results of several different palladium based catalysts for the conversion of PDX into 2-n-butoxyethanol (EB). All the runs were carried out at a reaction temperature of 200 degrees Celsius (473 degrees K) with a total reactor pressure of 300 psig (2068 kPa) and a target PDX feed rate of 13.5 grams/hr and a hydrogen feed rate of 700 standard cc/minute. The H2/PDX feed mole ratio was about 18/1. In all examples, 20 cc of catalyst material was packed as a bed in the unit described above. The total milligrams of Pd in each of the catalyst charges is also included for comparison. The table below records the results of runs using different catalysts in terms of grams of product recovered in four hours and a final % selectivity to the desired EB product based on converted PDX.

TABLE 2

| Run | Catalyst | mg Pd | % Conv. PDX | g EB | g DBE | g MBE | g EtButyr | g EG | % Selectivity To EB |
|---|---|---|---|---|---|---|---|---|---|
| 7 | A | 69 | 37 | 17.30 | 0.013 | 0.28 | 1.21 | 0.0 | 91.5 |
| 8 | B | 87 | 45 | 17.23 | 0.027 | 0.29 | 1.17 | 0.22 | 89.5 |
| 9 | C | 45 | 23 | 5.49 | 0.0 | 0.12 | 0.41 | 0.30 | 82.6 |
| 10 | D | 78 | 20 | 9.19 | 0.0 | 0.41 | 1.36 | 0.0 | 82.6 |
| 11 | E | 166 | 6 | 0.76 | 0.0 | 0.03 | 0.29 | 0.0 | 69 |
| 12 | F | 27 | 11 | 2.08 | 0.0 | 0.03 | 0.09 | 0.73 | 57.7 |

TABLE 2-continued

| Run | Catalyst | mg Pd | % Conv. PDX | g EB | g DBE | g MBE | g EtButyr | g EG | % Selectivity To EB |
|---|---|---|---|---|---|---|---|---|---|
| 13 | G | 75 | 94 | 27.26 | 11.23 | 1.00 | 0.80 | 1.89 | 67.1 |
| 14 | H | 135 | 99 | 25.31 | 16.95 | 0.30 | 0.62 | 6.85 | 49.75 |
| 15 | I | 132 | 99 | 24.62 | 16.19 | 0.51 | 0.70 | 6.12 | 50.6 |
| 16 | J | 78 | 80 | 30.07 | 1.00 | 0.45 | 0.13 | 1.39 | 81.2 |
| 17 | K | 175 | 97 | 24.42 | 12.42 | 1.13 | 3.68 | 4.62 | 52.1 |

The catalysts used in the above table are listed below:
A = Degussa 0.5% Pd/$^1/_{16}$" alumina spheres
B = Calsicat (Mallinckrodt Specialty Chemical Co.) 0.5% Pd/$^1/_{16}$" alumina spheres
C = Engelhard (BASF) 0.3% Pd/$^1/_{8}$" alumina spheres
D = Engelhard 1% Pd/$^1/_{8}$" silica "star" extrudates with MgO binder
E = Engelhard 2% Pd/$^1/_{8}$" silica "star" extrudates with MgO binder
F = Sud-Chemie ~0.2% Pd/Ag/$^1/_{8}$" alumina sphere "acetylene case catalyst" G-98B
G = Engelhard (BASF) 0.75% Pd/$^1/_{16}$" alumina extrudates E4126E
H = Engelhard (BASF) 1% Pd/$^1/_{16}$" alumina spheres AS-38
I = Engelhard (BASF) 1% Pd/$^1/_{8}$" alumina spheres AS-38 lot SEO 7473
J = Evonik 0.6% Pd/$^1/_{16}$" alumina spheres Noblyst 1513
K = Evonik 2% Pd/$^1/_{16}$" silicon dioxide extrudates product number 48.7823.4010

As may be seen from the table, the catalysts A-D may be considered as "moderate activity" catalysts and generally gave the highest selectivity to the desired product. Catalysts E and F are low activity catalysts. Catalysts G-K are high activity catalysts, of which catalyst J, having the lowest activity of that subgroup, as measured as % conversion of the acetal, also had the highest selectivity to desired product.

Comparative Example 1

Carbon Supports

Table 3 records data on the conversion of PDX into 2-n-butoxyethanol, by a bed of 1% Pd/granular carbon catalyst, BASF C 3655, 20 cc with a weight of catalyst of 7.83 grams. The carbon supported palladium catalyst generally was not selective to the desired 2-n-butoxyethanol product. The data below lists the average % PDX conversion and % selectivity to desired 2-n-butoxyethanol over the last four hours and the sum of grams of products during the last four hours. Ethylene glycol solvent and an acidic acid promoter were not added to the reaction mixture.

The last run –141 was carried out using nitrogen gas feed to demonstrate that the presence of hydrogen is required to prepare significant amounts of desired hydroxyl ether hydrocarbon product.

Comparative Examples 2 and 3

Use of the Catalyst Compositions of the Invention in a Liquid Phase Process

The comparison examples listed below are batch autoclave liquid phase PDX hydrogenation runs carried out using pulverized samples of catalysts of this invention. The two batch autoclave liquid phase hydrogenation examples are a direct comparison between the Evonik Degussa 0.5% Pd/Al2O3 catalyst and the BASF 1% Pd/C3655 carbon catalyst. In both cases the same amount of Pd catalytic metal (50 mgs) was present. The data below shows the differing behavior of catalysts employed in a liquid phase hydrogenolysis compared to the same catalysts used in a vapor phase hydrogenolysis, and that the suitability of the catalysts in the liquid phase hydrogenolysis cannot predict catalyst performance in a vapor phase process.

Comparative Example 2

Batch Autoclave Hydrogenation of
2-n-Propyl-1,3-Dioxolane (PDX) Using Ethylene Glycol Co-Solvent with a Pulverized BASF 1% Pd/Carbon Granules C 3655 Catalyst 1% Pd/Carbon catalyst as described in Comparative Example 1 was used to produce the examples listed above in

TABLE 3

| Run | P psig/kPa | Temp Celsius/ Kelvin | PDX g/hr | H2 sccm | % PDX Conv. | g EB Last 4 hrs | g DBE Last 4 hrs | g MBE Last 4 hrs | g EtButyr Last 4 hrs | g EG Last 4 hrs | % Selectivity to EB on converted PDX |
|---|---|---|---|---|---|---|---|---|---|---|---|
| 18 | 100/689 | 200/473 | 6.64 | 700 | 75 | 6.03 | 3.58 | 0.89 | 5.34 | 1.43 | 33.8 |
| 19 | 50/345 | 200/473 | 13.3 | 700 | 53 | 6.04 | 2.39 | 0.98 | 9.01 | 1.23 | 29.5 |
| 20 | 50/345 | 170/443 | 13.3 | 700 | 14 | 4.50 | 0.15 | 0.09 | 2.09 | 0.84 | 59.7 |
| 21 | 100/689 | 170/443 | 6.64 | 700 | 44 | 3.97 | 0.92 | 0.09 | 0.92 | 0.77 | 42.1 |
| 22 | 150/1034 | 170/443 | 6.64 | 700 | 54 | 6.80 | 2.16 | 0.07 | 1.02 | 1.27 | 57.6 |
| 23 | 50/345 | 170/443 | 6.64 | 700 | 40 | 4.97 | 1.00 | 0.12 | 1.95 | 0.82 | 53.2 |
| 24 | 150/1034 | 150/423 | 6.64 | 700 | 25 | 4.33 | 0.50 | 0.01 | 0.40 | 0.75 | 64.4 |
| 25 | 50 (N2) 345 kPa | 200/473 | 6.64 | 200 (N2) | 18 | 0.25 | 0.00 | 0.02 | 2.43 | 0.15 | 8.2 | this application. Six grams of BASF 1% Pd/carbon granules C 3655 were pulverized in a clean mortar and pestle and sieved to a powder of particles less than 50 mesh. Five grams (5.00 g) of this powder containing a total of 50 mg of palladium was charged to a 300 ml Autoclave Engineers magnetic drive Hastelloy B autoclave. A mixture of 20.0 grams of PDX and 100.0 grams of ethylene glycol co-solvent was prepared in a 250 ml beaker and mixed thoroughly and added to the autoclave base containing the pulverized palladium/carbon catalyst. The contents of the autoclave were mixed by stirring with a spatula. The autoclave head was placed on the base and the head bolts torqued to secure the autoclave base. The autoclave was then purged with nitrogen to displace any air. The autoclave was then pressured to 400 psig (2758 kPa) with hydrogen and the magnetic stirrer started. The autoclave was heated to 200 degrees Celsius (473 degrees K) and the pressure adjusted to 500 psig (3447 kPa). The reaction was permitted to run for 1 hour. Following this, the autoclave was cooled to ambient temperature and vented of its pressure. The contents of the autoclave were removed and the solid catalyst was removed from the liquid by filtration. The liquid product was then analyzed by normal gas chromatographic methods described previously. The liquid product contained: PDX 3.41 grams; 2-n-butoxyethanol 10.78 grams; 1,2-di-n-butoxyethane 0.30 grams; ethylene glycol 99.65 grams.

Comparative Example 3

Batch Autoclave Hydrogenation of 2-n-Propyl-1,3-Dioxolane (PDX) Using Ethylene Glycol Co-Solvent with a Pulverized Evonik Degussa 0.5% Pd/Alumina E Catalyst A sample (12 grams) of Evonik Degussa 0.5% Pd/1/16" Alumina sphere catalyst E was pulverized in a clean mortar and pestle to below 120 mesh powder. Ten (10.0) grams of this powdered catalyst containing 50 mg of palladium was added to the base of a 300 ml Autoclave Engineers magnetic drive Hastelloy B autoclave. A mixture of PDX (20.0 grams) and ethylene glycol (100.0 grams) co-solvent were prepared in a 250 ml beaker and mixed well and then added to the base of the autoclave. The contents in the autoclave were stirred with a spatula prior to placing the autoclave head on the base. After applying torque to the head bolts to secure the autoclave, it was purged with nitrogen to displace any air. The autoclave was pressured to 400 psig (2758 kPa) with hydrogen and heated with stirring to 200 degrees Celsius (473 degrees K). At 200 degrees C. (473 degrees K), the pressure was adjusted to 500 psig (3447 kPa) and the reaction was run for one hour. After the one hour period, the autoclave was cooled to ambient temperature and the pressure vented. The contents were removed and filtered. The filtration was difficult. A total of 88.4 grams of liquid product was recovered. The amount of compounds contained in this material was: PDX 6.0 grams, water 1.0 grams, ethylene glycol 81.4 grams, no 2-n-butoxyethanol product was observed.

Comparative Example 4

Catalysts Doped Lithium, Phosphoric Acid, or Ni

As mentioned previously, certain additives may be used to modify the performance of the catalysts of this invention. The unmodified Evonik Degussa catalyst of the examples below is considered to be a selective catalyst for the preparation of desired EB product but is of relatively low catalyst activity. The modifiers listed below were added by the generalized incipient wetness method described below for the purpose of increasing the activity of the catalyst while retaining desired selectivity to EB product:

Preparation of a Degussa 0.5% Pd/1/16" Alumina Sphere Catalyst Having 0.5 mmole of H3PO4/Gram of Catalyst by Incipient Wetness Method 0.88 grams of 85% aqueous phosphoric acid was added to a 250 milliliter round bottomed flask along with 7.0 ml of de-ionized water. This solution was chilled externally by a water ice bath. 20 cubic centimeters (14.04 grams) of Evonik Degussa 0.5% Pd/1/16" alumina sphere catalyst (E exp P/D lot 11 DJ022) was added to the flask and swirled rapidly to permit all pellets to absorb the dilute aqueous acid. A vacuum adapter was placed on the round bottomed flask and the cold wet pellets were subjected to 30 mm Hg pressure (4 kPa) by a vacuum pump for about 5 minutes. The pressure was then permitted to return to atmospheric pressure. This vacuum and repressuring was repeated twice more to mix the liquid into all pores of the catalyst. Following this, the pellets were swept with a stream of about 1 liter/minute of dry nitrogen for 48 hours to remove the water and leave behind the non-volatile acid. The net weight of final dry catalyst was 14.44 grams.

Table 4 below shows the effects of different additives to an Evonik Degussa 0.5% Pd/1/16" alumina sphere catalyst Eon the conversion of PDX into 2-n-butoxyethanol. All runs were carried out at 200 degrees Celsius (473 degrees K), 300 psig (2068 kPa), with 13.5 grams of PDX fed/hr with a H2/PDX feed mole ratio of about 18/1.

TABLE 4

| Run | Additive | mmole/g | % PDX Conv. | gram EB last 4 hr | gram DBE Last 4 hr | gram MBE Last 4 hr | gram EtButyr Last 4 hr | gram EG Last 4 hr | % Selectivity to EB |
|---|---|---|---|---|---|---|---|---|---|
| 26 | none | 0.0 | 29 | 10.14 | 0.0 | 0.24 | 0.65 | 0.38 | 85.6 |
| 27 | LiOAc | 0.05 | 23 | 6.65 | 0.19 | 0.07 | 0.25 | 0.31 | 86.1 |
| 28 | LiOAc | 0.5 | 9 | 2.44 | 0.0 | 0.14 | 0.57 | 0.0 | 75.9 |
| 29 | H3PO4 | 0.05 | 34 | 13.44 | 0.04 | 0.13 | 0.42 | 0.74 | 86.8 |
| 30 | H3PO4 | 0.5 | 75 | 23.02 | 7.32 | 0.14 | 0.07 | 4.03 | 64.1 |
| 31 | Ni(OAc)2 | 0.05 | 61 | 18.67 | 2.64 | 0.28 | 0.71 | 1.24 | 78.0 |

The results indicate that the addition of relatively basic lithium acetate retards the rate of reaction, especially at the relatively high 0.5 mmole/g loading. The addition of phosphoric acid increases PDX conversion rate but significantly promotes the formation of DBE above trace (0.05 mmole/gram) amounts of acid added. The addition of nickel increased PDX conversion even at trace amounts but significantly increased the formation of the undesired DBE co-product. These particular additives exhibited either a negative or very minor improvement on selectivity to desired EB product. The base metal modifier nickel in particular harmed desired selectivity by producing significant amounts of DBE at low nickel loadings.

Example 3

Catalysts Doped with Alkali Metals

Tables 5 and 6 below show effect of alkali metal acetate additives upon a highly active but relatively unselective 0.5% Pd/alumina catalyst, Johnson Matthey Type 310 trilobe extrudate. The original untreated catalyst had a surface area of 206 m2/gram of theta alumina. In one example where this same catalyst was treated with 0.05 mmole of potassium acetate/gram by incipient wetness technique, the surface area dropped to 122 m2/gram, in a second example also using the Johnson Matthey 310 catalyst with 0.05 mmole of potassium acetate/gram produced a catalyst having 133 m2/gram. While not wishing to be bound by theory, these additives may be changing the surface area of catalysts by reducing the number of accessible catalyst pores in addition to possibly changing the number of acidic sites present on the support, thereby changing the resulting performance of the catalyst. Table 5 shown below shows the effect of different alkali metal acetate additives on the selectivities to desired product EB and different undesired co-products at a hydrogen/PDX feed mole ratio of 150/1.

TABLE 5

Effect of M + (OAc—) Additives on JM 0.5% Pd/Al2O3 Type 310 Trilobe Catalyst At 150/1 H2/PDX Feed Ratio at 210 Deg C. @ 300 psig

| Run | Additive | mmole/g | EB prod Rate lb/ft3-hr | % PDX Conver. | % Sel EB | % Sel MBE | % Sel DBE | % Sel Ester | % Sel DB | % Sel Additional EG |
|---|---|---|---|---|---|---|---|---|---|---|
| 32 | none | 0.0 | 14.1 | 95.2 | 83.7 | 0.32 | 12.9 | 0.86 | 0.47 | 1.71 |
| 33 | CsOAc | 0.10 | 2.34 | 35 | 88.6 | 0.48 | 2.40 | 1.49 | 0.36 | 6.67 |
| 34 | CsOAc | 0.05 | 4.16 | 40 | 83.1 | 0.77 | 2.67 | 1.70 | 0.46 | 11.3 |
| 35 | CsOAc | 0.05 | 7.77 | 58 | 89.4 | 1.09 | 2.45 | 2.59 | 0.71 | 3.77 |
| 36 | RbOAc | 0.05 | 7.30 | 56 | 92.1 | 0.34 | 2.67 | 3.05 | 0.28 | 1.54 |
| 37 | KOAc | 0.05 | 10.07 | 67 | 91.6 | 0.51 | 4.29 | 2.58 | 0.28 | 0.78 |
| 38 | KOAc | 0.05 | 11.48 | 73 | 93.5 | 0.73 | 2.26 | 2.03 | 0.39 | 1.08 |
| 39 | NaOAc | 0.05 | 10.48 | 74 | 91.3 | 0.44 | 4.14 | 2.53 | 0.24 | 1.38 |

Note:
Runs having (*) were run at 230 degrees C.; % Selectivities based on converted PDX; EB = 2-n-butoxyethanol; MBE = methyl n-butyl ether; DBE = 1,2-di-n-butoxyethane; Ester = ethyl butyrate and EB butyrate; DB = mono-n-butyl ether of Diethylene glycol; Additional EG = unaccountable ethylene glycol that can't be accounted for by formation of DBE. PDX feed rate 6.7 grams/hr.

Example 4

Catalysts Doped with Alkali Metals Increasing the Hydrogen:PDX Molar Ratio

Using the procedure in Example 3, Table 6 shows the effects of these additives upon the Johnson Matthey Type 310 Trilobe catalyst when the hydrogen/PDX feed mole ratio was adjusted to 55:1.

TABLE 6

Effect of M + (OAc—) Additives on JM 0.5% Pd/Al2O3 Type 310 Trilobe Catalyst At 55/1 H2/PDX Feed Ratio at 210 Deg C. @ 300 psig

| Run | Additive | mmole/g | EB prod Rate lb/ft3-hr | % PDX Conver. | % Sel EB | % Sel MBE | % Sel DBE | % Sel Ester | % Sel DB | % Sel Additional EG |
|---|---|---|---|---|---|---|---|---|---|---|
| 40 | none | 0.0 | 23.6 | 85 | 68.5 | 0.56 | 25.7 | 1.46 | 0.14 | 3.62 |
| 41 | CsOAc | 0.05 | 9.78 | 38 | 84.0 | 1.77 | 2.50 | 2.96 | 0.48 | 8.25 |
| 42 | RbOAc | 0.05 | 9.51 | 32 | 87.0 | 0.57 | 3.01 | 6.04 | 0.23 | 3.18 |
| 43 | KOAc | 0.05 | 14.98 | 44 | 88.1 | 0.53 | 5.06 | 4.19 | 0.18 | 1.98 |
| 44 | KOAc | 0.05 | 14.69 | 46 | 88.5 | 1.45 | 3.39 | 2.97 | 0.27 | 3.47 |
| 45 | NaOAc | 0.05 | 17.69 | 56 | 88.3 | 0.41 | 5.64 | 3.81 | 0.18 | 1.67 |

Notes are the same as for table 5; PDX feed rate 13.5 grams/hr.

The data in Examples 3 and 4 shows that the addition of alkali metal acetate to the moderately selective JM catalyst increased selectivity to the desired EB product. This is most strongly observed by the reduction of DBE co-product a high boiling co-product of little value, with cesium having the most significant impact on DBE formation. The data also demonstrates the overall desired performance of the vapor phase process for not making significant amounts of DB, which is a major co-product of ethylene oxide based traditional processes to prepare EB. The data of these tables also indicates that sodium and potassium are effective and desirable as they give a combination of good selectivity to EB product with the smallest drop in catalytic activity.

Example 5

Catalysts Doped with Alkaline Earth Metals

Alkaline earth metals are effective modifiers for improving the desired selectivity of a relatively active but moderately selective catalyst. The tables below list the results of alkaline earth acetate additive upon the JM Type 310 Trilobe catalyst at 150:1 (Table 7) and 55:1 (Table 8) hydrogen to PDX feed mole ratios using the hydrogenolysis unit.

The alkaline earth additives show a similar performance trend to that observed in the alkali metal series. In this case, barium appears to be the favored metal of this series for obtaining the highest selectivity to EB product as an additive. As in the case with the alkali metal acetate series, the alkaline earth acetate series has the greatest impact on suppression of the DBE co-product with the largest cation, namely barium exhibiting the greatest effect at a given concentration and reaction temperature. In this series, barium and strontium are the preferred alkaline earth additives to give the best combination of selectivity and good production rate. Further, the data shows that a higher amount of the divalent cation additive is required to achieve a similar percent selectivity to EB than the corresponding mono-valent cations of the alkali metal acetate series. As observed in the alkali metal case, very little DB co-product is produced. In both the alkali metal and alkaline earth acetate additive cases, higher H2/PDX feed mole ratios favor higher selectivity to desired EB product.

Example 6

Catalysts Doped with Alkali Metal Fluorides

The use of alkali metal fluorides, in particular potassium fluoride, have been reported to modify aluminum oxide supports in a manner to make them basic for purposes of carrying out aldol condensation and other types of similar reactions as reported by G. W. Kabalka et al *Tetrahedron* 1997, 83, 7999 and references therein. Table 9 shown below lists the effect of treatment of a highly active but relatively unselective catalyst, namely Johnson Matthey 0.5% Pd/Al2O3 Type 310 Trilobe catalyst, with different alkali metal fluoride additives. The reaction conditions were 210 degrees Celsius at 300 psig with a hydrogen/PDX feed mole ratio of 150/1.

TABLE 7

Effect of M(+2) (OAc—)2 Additives on JM 0.5% Pd/Al2O3 Type 310 Trilobe Catalyst At 150/1 H2/PDX Feed Ratio at 210 Deg C. @ 300 psig

| Run | Additive | mmole/g | EB prod rate LbEB/ft3-hr | PDX % Conver. | % Sel EB | % Sel MBE | % Sel DBE | % Sel Ester | % Sel DB | % Sel Additional EG |
|---|---|---|---|---|---|---|---|---|---|---|
| 46 | none | 0.0 | 14.4 | 95.2 | 83.7 | 0.32 | 12.9 | 0.86 | 0.47 | 1.71 |
| 47 | Ba(OAc)2 | 0.025 | 15.23 | 90 | 88.3 | 0.45 | 9.24 | 0.97 | 0.72 | 0.72 |
| 48 | Ba(OAc)2 | 0.05 | 14.85 | 90 | 90.8 | 0.53 | 5.85 | 2.72 | 0.23 | −0.09 |
| 49 | Ba(OAc)2 | 0.10 | 13.61 | 80 | 90.6 | 0.58 | 6.14 | 2.53 | 0.14 | −0.21 |
| 50 | Ca(OAc)2 | 0.05 | 14.12 | 89 | 88.3 | 0.33 | 8.02 | 2.70 | 0.23 | 0.54 |
| 51 | Mg(OAc)2 | 0.05 | 16.38 | 99 | 85.7 | 0.76 | 10.34 | 2.50 | 0.67 | −0.69 |

Notes are the same as for Table 5; PDX feed rate 6.7 grams/hr

TABLE 8

Effect of M(+2)(OAc—)2 Additives on JM 0.5% Pd/Al2O3 Type 310 Trilobe Catalyst At 55/1 H2/PDX Feed Ratio at 210 Deg C. @ 300 psig

| Run | Additive | mmole/g | EB prod rate lb/EB/ft3-hr | PDX % Conver. | % Sel EB | % Sel MBE | % Sel DBE | % Sel Ester | % SEl DB | % Sel Additional EG |
|---|---|---|---|---|---|---|---|---|---|---|
| 52 | none | 0.0 | 23.59 | 85 | 68.5 | 0.56 | 25.7 | 1.46 | 0.14 | 3.62 |
| 53 | Ba(OAc)2 | 0.025 | 30.53 | 95 | 81.1 | 1.08 | 14.84 | 1.89 | 0.47 | 0.66 |
| 54 | Ba(OAc)2 | 0.05 | 25.77 | 77 | 85.9 | 0.61 | 8.90 | 3.81 | 0.15 | 0.65 |
| 55 | Ba(OAc)2 | 0.05 | 29.42 | 85 | 86.3 | 0.76 | 8.40 | 3.89 | 0.19 | 0.47 |
| 56 | Ba(OAc)2 | 0.10 | 20.76 | 58 | 87.6 | 0.46 | 6.92 | 3.74 | 0.12 | 1.15 |
| 57 | Ca(OAc)2 | 0.05 | 23.86 | 74 | 83.4 | 0.32 | 10.27 | 4.11 | 0.16 | 1.71 |
| 58 | Mg(OAc)2 | 0.05 | 29.25 | 92 | 80.9 | 0.64 | 14.02 | 3.91 | 0.37 | 0.20 |

Notes are the same as for Table 5, runs with (*) carried out at 230 deg Celsius; run with (**) carried out at 220 deg Celsius; PDX feed rate 13.5 grams/hr

TABLE 9

Effect of 0.05 mmole M(+)F(−)/gram Upon JM 0.5%
Pd/Al2O3 Type 310 Trilobe Catalyst lot #10527 At
210 Degree Celsius at 150/1 H2/PDX Feed Mole Ratio at 300 psig

| Run | Additive | EB Prod Lb/ft3-hr | % PDX Conver. | % Sel EB | % Sel MBE | % Sel DBE | % Sel Ester | % Sel DB | % Sel Additional EG |
|---|---|---|---|---|---|---|---|---|---|
| 59 | none | 15.6 | 97 | 88.1 | 0.82 | 7.75 | 2.70 | 0.62 | −0.08 |
| 60 | CsF | 3.72 | 36 | 79.6 | 1.33 | 11.45 | 5.14 | 0.26 | 2.27 |
| 61 | KF | 7.62 | 50 | 91.8 | 0.37 | 2.27 | 3.78 | 0.28 | 1.50 |
| 62 | NaF | 13.89 | 81 | 91.8 | 0.26 | 4.86 | 1.99 | 0.18 | 0.96 |
| 63 | LiF | 15.92 | 93 | 89.3 | 0.33 | 7.86 | 1.93 | 0.23 | 0.36 |

Notes same as in table 5; PDX feed rate 6.7 grams/hr

Example 7

Catalysts Doped with Alkali Metal Fluorides

Table 10 shows the effect of changing the hydrogen/PDX feed ratio to 55/1 at the same conditions with the same catalysts of Example 6.

TABLE 10

Effect of 0.05 mmole M(+)F(−)/gram Upon JM 0.5%
Pd/Al2O3 Type 310 Trilobe Catalyst lot #10527 At
210 Degrees Celsius at 55/1 H2/PDX Feed Mole Ratio at 300 psig

| Run | Additive | EB Prod Lb/ft3-hr | % PDX Conver. | % Sel EB | % Sel MBE | % Sel DBE | % Sel Ester | % Sel DB | % Sel Additional EG |
|---|---|---|---|---|---|---|---|---|---|
| 64 | none | 29.3 | 95 | 78.7 | 0.81 | 16.77 | 3.24 | 0.38 | 0.08 |
| 65 | CsF | 4.08 | 20 | 64.9 | 2.37 | 20.5 | 9.10 | 0.25 | 2.82 |
| 66 | KF | 8.06 | 32 | 84.9 | 0.44 | 2.76 | 7.54 | 0.23 | 4.16 |
| 67 | NaF | 19.80 | 60 | 87.7 | 0.35 | 6.49 | 3.59 | 0.16 | 1.71 |
| 68 | LiF | 24.83 | 75 | 84.2 | 0.38 | 11.03 | 3.03 | 0.15 | 1.18 |

Notes same as in table 5; PDX feed rate 13.5 gram/hr

As was observed with the alkali metal acetate additives, a trend is observed with the alkali metal fluoride additives where activity, as measured by the percent PDX conversion, is observed to increase as the alkali metal cation size decreases from Cs+ down to the smallest ion Li+. However, the Cs metal fluoride is the poorer additive at improving selectivity to EB product as can be seen from the high production of undesired DBE co-product. Also apparent with the alkali metal fluoride additive cases is the combination of high selectivity to EB product while retaining good production rate as exhibited with the sodium fluoride case. By contrast, sodium and potassium acetates were essentially equivalent. Further, lithium acetate did not appear to contribute to an improvement in selectivity, while lithium fluoride results showed a marked improvement in selectivity toward the production of EB. These observations are an indication that the two anion classes do participate in affecting the selectivity of the catalyst as do the metal cations.

Example 8

Varying the Anions of K Doped Catalysts

Table 11 shows the effect on selectivity by varying those anions of potassium additives with acetate, chloride or fluoride. The examples were carried out at 0.05 mmole additive/gram of catalyst at 210 degrees Celsius at 300 psig. Two different hydrogen/PDX feed ratios are given. While potassium acetate is generally considered to be a mild base and potassium chloride a neutral salt, the data below indicates that the potassium acetate and chloride perform in a similar manner unlike the fluoride cases.

TABLE 11

Effect of Different Anions of K(+) Additives Upon JM 0.5% Pd/"Al2O3 Type 310
Trilobe Catalyst At 210 Degrees Celsius at 300 Psig at 0.05 mmole/gram K(+) Loading

| Run | K Cpd | H2/PDX MR | EB Prod lbEB/ft3-hr | % PDX Conver. | % Sel EB | % Sel DBE | % Sel MBE | % Sel Ester | % Sel DB | % Sel Additional EG |
|---|---|---|---|---|---|---|---|---|---|---|
| 69 | none | 150 | 15.6 | 97 | 88.1 | 7.75 | 0.82 | 2.70 | 0.62 | −0.08 |
| 70 | KOAc | 150 | 10.1 | 67 | 91.6 | 4.29 | 0.51 | 2.58 | 0.28 | 0.78 |
| 71 | KCl | 150 | 13.1 | 77 | 90.6 | 4.12 | 0.69 | 4.19 | 0.43 | −0.03 |
| 72 | KF | 150 | 7.62 | 50 | 91.8 | 2.27 | 0.37 | 3.78 | 0.23 | 1.50 |
| 73 | none | 55 | 29.3 | 95 | 78.7 | 16.8 | 0.81 | 3.24 | 0.38 | 0.08 |

TABLE 11-continued

Effect of Different Anions of K(+) Additives Upon JM 0.5% Pd/'Al2O3 Type 310
Trilobe Catalyst At 210 Degrees Celsius at 300 Psig at 0.05 mmole/gram K(+) Loading

| Run | K Cpd | H2/PDX MR | EB Prod lbEB/ft3-hr | % PDX Conver. | % Sel EB | % Sel DBE | % Sel MBE | % Sel Ester | % Sel DB | % Sel Additional EG |
|---|---|---|---|---|---|---|---|---|---|---|
| 74 | KOAc | 55 | 15.0 | 44 | 88.1 | 5.06 | 0.53 | 4.19 | 0.18 | 1.98 |
| 75 | KCl  | 55 | 17.0 | 51 | 85.6 | 4.45 | 0.75 | 7.04 | 0.28 | 1.86 |
| 76 | KF   | 55 | 8.06 | 32 | 85.0 | 2.76 | 0.44 | 7.54 | 0.23 | 4.16 |

Notes same as in Table 5; PDX feed rate at 150/1 = 6.7 grams/hr; PDX feed rate at 55/1 = 13.5 grams/hr

Example 9

TOPO Doped Catalysts

Certain Lewis bases, a class of compounds that bind to acid sites without the formation of conjugate acids such as water or acetic acid, have the ability to modify highly active, but relatively unselective hydrogenation catalyst to suppress the formation of undesired DBE co-product. Table 12 below shows the effect of 0.05 mmole of TOPO (tri-n-octylphosphine oxide)/gram upon Johnson Matthey 0.5% Pd/Al2O3 Type 310 Trilobe. The TOPO modified catalyst was prepared using an incipient wetness method that used 1,4-dioxane solvent in place of water.

TABLE 12

Effect of 0.05 mmole TOPO/gram Upon JM 0.5% Pd/Al2O3 Type
310 Trilobe Catalyst At 210 Degrees Celsius at 300 psig

| Run# | mmole TOPO/g | H2/PDX MR | Prod EB lb/ft3-hr | % PDX Conver. | % Sel EB | % Sel DBE | % Sel MBE | % Sel Ester | % Sel DB | % Sel Additional EG |
|---|---|---|---|---|---|---|---|---|---|---|
| 77 | 0.0  | 150 | 15.6 | 97 | 88.1 | 7.75 | 0.82 | 2.70  | 0.62 | −0.08 |
| 78 | 0.0  | 55  | 29.3 | 95 | 78.7 | 16.8 | 0.81 | 3.24  | 0.38 | 0.08 |
| 79 | 0.05 | 150 | 3.55 | 27 | 87.8 | 1.21 | 0.13 | 5.17  | 0.48 | 5.22 |
| 80 | 0.05 | 55  | 5.14 | 18 | 78.0 | 0.64 | 0.21 | 10.99 | 0.37 | 9.79 |

Notes same as in Table 5; PDX feed rate at 150/1 = 6.7 grams/hr; PDX feed rate at 55/1 = 13.5 grams/hr While this particular additive lowered the catalytic activity, it greatly reduced the formation of the undesired co-product DBE demonstrating the ability to modify the catalyst in a manner to control unwanted co-products using Lewis base materials.

Comparative Example 5

Catalysts Doped with Conventional Modifiers

The following Table 13 shows the effect of controlled poisoning of a highly active but relatively unselective catalyst with known poisons to palladium hydrogenation catalysts in an attempt to attain higher selectivity to desired EB product. Selective catalyst poisoning of palladium with the metals lead, silver and tin have been employed in the art for selective hydrogenation of acetylene and other highly active substrates in the presence of ethylene to achieve higher hydrogenation efficiency. The table below indicates that this type of additive is not desirable for use on the catalysts of this invention.

TABLE 13

Comparative Examples
Effect of Different Metal Poisons Upon JM 0.5% Pd/Al2O3 Type 310 Trilobe
Catalyst At 210 Degrees Celsius at 150/1 H2/PDX Feed MR at 300 psig

| Run | Metal | M/Pd M.R. | Prod EB lb/ft3-hr | % PDX Conver. | % Sel EB | % Sel DBE | % Sel MBE | % Sel Ester | % Sel DB | % Sel Additional EG |
|---|---|---|---|---|---|---|---|---|---|---|
| 81 | none | 0.0   | 14.4  | 95 | 83.7 | 12.9 | 0.32 | 0.86 | 0.47 | 1.71 |
| 82 | Sn   | 0.1/1 | 14.88 | 98 | 82.8 | 15.1 | 0.42 | 1.20 | 0.51 | −0.41 |
| 83 | Pb   | 0.1/1 | 15.19 | 99 | 79.7 | 17.1 | 0.32 | 0.94 | 0.54 | 1.44 |
| 84 | Ag   | 0.1/1 | 14.82 | 97 | 80.4 | 15.6 | 0.31 | 0.98 | 0.53 | 2.10 |
| 85 | Pb   | 0.5/1 | 3.0   | 34 | 73.2 | 6.06 | 0.47 | 6.64 | 1.10 | 12.53 |

Comparative Examples 6

Other Noble Metals Loaded onto Supports

We have found that palladium is the noble metal catalyst for use in the process of the invention. Table 14 lists other noble metal catalyst systems and their performance as applied to this invention in a vapor phase hydrogenolysis unit.

TABLE 14

Comparative Examples
Palladium vs Other Noble Metal Catalysts at 210 Deg Celsius at 300 Psig

| Run# | Metal | %/wt | H2/PDX Feed MR | Prod EB lb/ft3-hr | % PDX Conver. | % Sel EB | % Sel DBE | % Sel MBE | % Sel Ester | % Sel DB | % Sel Additional EG |
|---|---|---|---|---|---|---|---|---|---|---|---|
| 86 | Pd/Al2O3 | 0.5 | 150 | 5.12 | 40 | 95.5 | 1.26 | 1.02 | 2.14 | 0.16 | −0.1 |
| 87 | Pd/Re(1/1) Al2O3 | 0.5 (Pd) | 150 | 4.13 | 58 | ~65 | 3.25 | 1.88 | 2.26 | 0.01 | 3.97(*) |
| 88 | Pd/Al2O3 | 0.5 | 55 | 7.58 | 26 | 90.8 | 1.38 | 1.02 | 4.52 | 0.12 | 2.14 |
| 89 | Ru/Al2O3 | 2.0 | 55 | 0.0 | 99.6 | 0.0 | 0.0 | 0.0 | 0.0 | 0.0 | 0.0(**) |
| 90 | Pt/Al2O3 | 0.3 | 55 | 2.55 | 17 | 56.7 | 2.75 | 0.41 | 1.73 | 0.77 | 37.7 |

Notes:
a) Evonik 0.5% Pd/$^1\!/_{16}$ alumina catalyst used, run 026 used same catalyst treated with 1/1 mole ratio of Pd/NH4 ReO4 by incipient wetness.
b) Engelhard catalyst
c) Alfa Aesar catalyst
(*)much butanol and other unknown co-products formed
(**)Only condensable product was water Example 10

Varying Surface Area of Supports and Types of Supports

Table 15 compares the catalysts of this invention with other support examples using the vapor phase hydrogenolysis unit.

TABLE 15

Comparison of Desired Alumina and Zirconia Supports vs Other Supports Palladium
Catalyzed at 210 Degrees Celsius at 300 psig at 150/1 H2/PDX Feed Mole Ratio

| Run | Support | % Pd/wt | BET m2/g | Prod EB lb/ft3-hr | % PDX Conver. | % Sel EB | % Sel DBE | % Sel MBE | % Sel Ester | % Sel DB | % Sel Additional EG |
|---|---|---|---|---|---|---|---|---|---|---|---|
| 91 | Gam Al2O3 | 0.5 | 260 | 5.12 | 40 | 95.9 | 1.26 | 1.02 | 2.14 | 0.16 | 0.0 |
| 92 | Alp Al2O3 | 0.35 | 3-7 | 10.5 | 66 | 93.1 | 2.3 | 0.40 | 1.50 | na | na |
| 93 | Alp Al2O3 | 0.5 | 5.7 | 16.7 | 98 | 89.4 | 5.79 | 0.91 | 3.85 | 0.04 | −0.32 |
| 94 | ZrO2 | 0.5 | 51 | 7.56 | 54 | 90.1 | 6.52 | 2.01 | 0.92 | 0.42 | −3.1 |
| 95 | ZrO2 | 0.25 | 51 | 6.07 | 55 | 92.3 | 1.51 | 0.95 | 4.80 | 0.46 | −0.67 |
| 96 | ZrO2 | 0.5 | 90 | 11.38 | 82 | 76.3 | 16.25 | 3.54 | 3.77 | 0.14 | −5.9 |
| 97 | AnaTiO2 | 0.5 | 37 | 4.37 | 50 | 64.6 | 28.6 | 0.17 | 0.92 | 0.53 | 5.1 |
| 98 | SiO2 | 2 | — | 21.3 | 74 | 73.1 | 23.3 | 0.23 | 2.01 | 0.0 | 1.36 |
| 99 | 80/20 Al2O3/SiO2 | 0.5 | 14.2 | 8.54 | 90 | 48.1 | 42.4 | 0.34 | 3.59 | 0.43 | 5.1 |

While not wishing to be bound by theory, but from our observations, the formation of the undesired diether DBE is a major yield loss of this particular reaction to prepare EB. It is speculated that acidic catalyst sites in combination with high support surface area may be major factors in the formation of DBE.

Example 11

Effect of Silica on Selectivity

Silica and silica/alumina catalysts are noteworthy as being known as acidic catalyst supports. The following table 16 lists the performance of different alumina catalysts of known properties as applied to the conversion of PDX into EB in accordance with this invention.

TABLE 16

Properties of Alumina Supports vs. Production Rate and % Selectivity to EB Product from PDX At 210 Degrees Celsius at 300 psig at 150/1 H2/PDX Feed Mole Ratio

| Run | Catalyst Support name | Type Al2O3 | BET m2/gram | % SiO2/wt | % Pd/wt | Prod EB lb/ft3-hr | % PDX Conver. | % Sel EB | % Sel DBE |
|---|---|---|---|---|---|---|---|---|---|
| 100 | Degussa | gamma | 227 | na | 0.5 | 9.06 | 56 | 93.3 | 2.16 |
| 101 | Evonik | gamma | 260 | na | 0.5 | 5.12 | 40 | 95.9 | 1.26 |
| 102 | Alfa Aesar | alpha | 0.82 | na | 0.5 | 2.58 | 26 | 89.5 | 2.33 |
| 103 | Alfa Aesar | alpha | 0.82 | na | 0.25 | 4.04 | 41 | 88.9 | 4.92 |
| 104 | Alfa Aesar | alpha | 3-7 | na | 0.35 | 10.5 | 66 | 93.1 | 2.3 |
| 105 | SAS-10 | na | 10 | na | 0.5 | 3.08 | 25 | 86.8 | 5.62 |
| 106 | SAS-10 | na | 10 | na | 0.25 | 3.73 | 25 | 83.6 | 8.54 |
| 107 | Alfa Aesar | na | 30 | 17.9 | 0.5 | 8.23 | 85 | 57.8 | 34.8 |
| 108 | Norpro SA3232 | alpha | 28.6 | 19 | 0.5 | 10.23 | 52 | 58.9 | 31.3 |
| 109 | Norpro SA51161 | alpha | 4.5 | <1 | 0.5 | 12.78 | 90 | 78.9 | 12.34 |
| 110 | Norpro SA52124 | alpha | 5.7 | <0.1 | 0.5 | 16.7 | 98 | 89.4 | 5.79 |
| 111 | Norpro SA3235 | Alp/theta | 14.2 | 19 | 0.5 | 8.54 | 90 | 48.1 | 42.4 |
| 112 | Norpro SA31145 | >99% theta | 69.8 | <0.3 | 0.5 | 11.25 | 99 | 62.8 | 30.9 |
| 113 | Norpro SA3177 | Alp/theta >98% | 93 | 0.1 | 0.5 | 12.27 | 98 | 62.8 | 30.8 |

What we claim is:

1. A process comprising a hydrogenolysis of cyclic compounds by contacting hydrogen with a cyclic compound comprising a cyclic acetal, a cyclic ketal, or a combination thereof in the vapor phase and in the presence of a catalyst composition to produce hydroxy ether mono-hydrocarbon compounds having at least one ether linkage and at least one primary hydroxyl group, wherein said catalyst composition comprises an α-aluminum oxide support containing or on which is deposited:
   a. palladium in an amount of up to 1 wt % based on the weight of the catalyst composition, and
   b. up to 1 wt % silicon dioxide based on the weight of the catalyst composition, wherein the BET surface area of the support is less than 30 m2/g.

2. The process of claim 1, wherein the BET surface area ranges from 0.2 m2/g to 15 m2/g.

3. The process of claim 1, wherein the BET surface area ranges from 0.2 m2/g to 8 m2/g.

4. The process of claim 1, wherein palladium is present in an amount of up to 0.7 wt %.

5. The process of claim 1, wherein silicon dioxide, if present in the catalyst composition, does not exceed 0.2 wt %.

6. The process of claim 1, wherein palladium is present in an amount of 0.2 wt % up to 0.7 wt %.

7. The process of claim 1, wherein the α-alumina support has an alpha phase content of at least 99%.

8. The process of claim 1, wherein the catalyst composition comprises:
   a. palladium in an amount of up to 0.7 wt % based on the weight of the catalyst composition, and
   b. if present, silicon dioxide, in an amount not to exceed 0.2 wt %, and wherein the BET surface area of the support is less than 10 m2/g.

9. The process of claim 1, wherein the catalyst composition further contains or to which is added a modifier, other than lithium acetate, comprising an alkali metal, an alkaline earth metal, or an organophosphine oxide compound.

10. A process comprising a hydrogenolysis of cyclic compounds by contacting hydrogen with a cyclic compound comprising a cyclic acetal, a cyclic ketal, or a combination thereof in the vapor phase and in the presence of a catalyst composition to produce hydroxy ether mono-hydrocarbon compounds having at least one ether linkage and at least one primary hydroxyl group, wherein said catalyst composition comprises an γ-aluminum oxide support containing or on which is deposited:
   a. palladium in an amount of up to 1 wt % based on the weight of the catalyst composition, and
   b. up to 1 wt % silicon dioxide based on the weight of the catalyst composition, wherein the BET surface area of the support is within a range of 100 m2/g-350 m2/g; and wherein the selectivity to the hydroxy ether mono-hydrocarbon compounds is at least 80 mole %.

11. The process of claim 10, wherein the BET surface area ranges from 150 m2/g to 300 m2/g.

12. The process of claim 10, wherein the BET surface area ranges from 200 m2/g to 300 m2/g.

13. The process of claim 10, wherein palladium is present in an amount of up to 0.7 wt %.

14. The process of claim 10, wherein silicon dioxide, if present in the catalyst composition, does not exceed 0.2 wt %.

15. The process of claim 10, wherein palladium is present in an amount of 0.2 wt % up to 0.7 wt %.

16. The process of claim 10, wherein the γ-alumina support has a gamma phase content of at least 99%.

17. The process of claim 10, wherein the catalyst composition comprises:
   a. palladium in an amount of up to 0.7 wt % based on the weight of the catalyst composition, and
   b. the amount of silicon dioxide, if present, does not exceed 0.2 wt %.

18. The process of claim 1, wherein the catalyst composition further contains or to which is added a modifier, other than lithium acetate, comprising an alkali metal, an alkaline earth metal, or a organophosphine oxide compound.

19. A process comprising a hydrogenolysis of cyclic compounds by contacting hydrogen with a cyclic compound comprising a cyclic acetal, a cyclic ketal, or a combination thereof in the vapor phase and in the presence of a catalyst composition to produce hydroxy ether mono-hydrocarbon compounds having at least one ether linkage and at least one primary hydroxyl croup, wherein said catalyst composition comprises a zirconium oxide support containing or on which is deposited:

a. palladium in an amount of up to 1 wt % based on the weight of the catalyst composition, and
b. up to 1 wt % silicon dioxide based on the weight of the catalyst composition, wherein the BET surface area of the support ranges from 0.2 m2/g to 100 m2/g.

20. The process of claim 19, wherein the BET surface area is within a range from 10 m2/g to 90 m2/g.

21. The process of claim 19, wherein the BET surface area is within a range from 25 m2/g to 70 m2/g.

22. The process of claim 19, wherein palladium is present in an amount of up to 0.7 wt %.

23. The process of claim 19, wherein silicon dioxide, if present in the catalyst composition, does not exceed 0.2 wt %.

24. The process of claim 19, wherein palladium is present in an amount of 0.2 wt % up to 0.7 wt %.

25. The process of claim 19, wherein silicon dioxide, if present in the catalyst composition, does not exceed 0.1 wt %.

26. The process of claim 19, wherein the catalyst composition comprises:
a. palladium in an amount of up to 0.7 wt % based on the weight of the catalyst composition, and
b. the amount of silicon dioxide, if present, does not exceed 0.2 wt %.

27. The process of claim 19, wherein the catalyst composition further contains or to which is added a modifier, other than lithium acetate, comprising an alkali metal, an alkaline earth metal, or a organophosphine oxide compound.

28. A process comprising a hydrogenolysis of cyclic compounds by contacting hydrogen with a cyclic compound comprising a cyclic acetal, a cyclic ketal, or a combination thereof in the vapor phase and in the presence of a catalyst composition to produce hydroxy ether mono-hydrocarbon compounds having at least one ether linkage and at least one primary hydroxyl group, wherein said catalyst composition comprises an aluminum oxide support containing or on which is deposited:
(i) palladium in an amount of up to 1 wt %, and
(ii) a modifier other than lithium acetate doped on said support, said modifier comprising an alkali metal, alkaline earth metal, or an organophosphine oxide compound.

29. The process of claim 28, wherein a modifier comprising potassium acetate, sodium acetate, cesium acetate, rubidium acetate, barium acetate, calcium acetate, magnesium acetate, lithium fluoride, sodium fluoride, potassium fluoride, calcium fluoride sodium chloride, potassium chloride, or calcium chloride is deposited onto the support.

30. The process of claim 28, wherein the modifier comprises sodium acetate, potassium acetate, barium acetate, or sodium fluoride.

31. The process of claim 28, wherein the modifier other than lithium acetate comprises an alkali metal or an alkaline earth metal.

32. The process of claim 28, wherein silicon dioxide, if present in the catalyst composition, does not exceed 0.2 wt %.

33. The process of claim 32, wherein the alumina support has an alpha phase content of at least 99% and the BET surface area ranges from 0.2 m2/g to 15 m2/g.

34. The process of claim 33, wherein palladium is present in an amount of up to 0.7 wt %.

35. The process of claim 28, wherein the modifier other than lithium acetate comprises an alkali metal or an alkaline earth metal.

36. The process of claim 35, wherein silicon dioxide, if present in the catalyst composition, does not exceed 0.2 wt %; the alumina support has an alpha phase content of at least 99%, the BET surface area of the support ranges from 0.2 m2/g to 15 m2/g, and palladium is present in an amount of up to 0.7 wt %.

37. A process comprising a hydrogenolysis of cyclic compounds by contacting hydrogen with a cyclic compound comprising a cyclic acetal, a cyclic ketal, or a combination thereof in the vapor phase and in the presence of a catalyst composition to produce hydroxy ether mono-hydrocarbon compounds having at least one ether linkage and at least one primary hydroxyl croup, wherein said catalyst composition comprises a zirconium oxide support containing or on which is deposited:
(i) palladium in an amount of up to 1 wt %, and
(ii) a modifier other than lithium acetate comprising an alkali metal, alkaline earth metal, or an organophosphine oxide compound.

38. The process of claim 37, wherein the modifier other than lithium acetate comprises an alkali metal or an alkaline earth metal.

39. The process of claim 37, wherein a modifier comprising potassium acetate, sodium acetate, barium acetate, calcium acetate, lithium fluoride, sodium fluoride, sodium chloride, potassium fluoride, potassium chloride, calcium fluoride, or calcium chloride is deposited onto the support.

40. The process of claim 37, wherein the modifier comprises sodium acetate, potassium acetate, barium acetate, or sodium fluoride.

41. The process of claim 37, wherein silicon dioxide, if present in the catalyst composition, does not exceed 0.2 wt %.

42. The process of claim 40, wherein the BET surface area ranges from 0.2 m2/g to 15 m2/g.

43. The process of claim 41, wherein palladium is present in an amount of up to 0.7 wt %.

44. The process of claim 37, wherein the modifier other than lithium acetate comprises an alkali metal or an alkaline earth metal.

45. The process of claim 44, wherein silicon dioxide, if present in the catalyst composition, does not exceed 0.2 wt %.

46. The process of claim 1, wherein selectivity to the production of hydroxy ether mono-hydrocarbons in the process is at least 86%.

47. The process of claim 46, wherein the selectivity is at least 90%.

48. The process of claim 47, wherein the molar ratio of hydrogen to cyclic compounds is at least 100:1.

49. The process of claim 47, wherein the selectivity is at least 94%.

50. The process of claim 46, wherein the selectivity is at least 90%.

51. The process of claim 47, wherein the molar ration of hydrogen to cyclic compounds is at least 100:1.

52. The process of claim 10, wherein selectivity to the production of hydroxy ether mono-hydrocarbons in the process is at least 86%.

53. The process of claim 52, wherein the selectivity is at least 90%.

54. The process of claim 53, wherein the molar ratio of hydrogen to cyclic compounds is at least 100:1.

55. The process of claim 19, wherein selectivity to the production of hydroxy ether mono-hydrocarbons in the process is at least 86%.

56. The process of claim 55, wherein the selectivity is at least 90%.

57. The process of claim 56, wherein the molar ratio of hydrogen to cyclic compounds is at least 100:1.

58. The process of claim 28, wherein selectivity to the production of hydroxy ether mono-hydrocarbons in the process is at least 86%.

59. The process of claim 58, wherein the selectivity is at least 90%.

60. The process of claim 59, wherein the molar ratio of hydrogen to cyclic compounds is at least 100:1.

61. The process of claim 37, wherein selectivity to the production of hydroxy ether mono-hydrocarbons in the process is at least 86%.

62. The process of claim 61, wherein the selectivity is at least 90%.

63. The process of claim 62, wherein the molar ratio of hydrogen to cyclic compounds is at least 100:1.

* * * * *